US012576050B2

(12) United States Patent (10) Patent No.: US 12,576,050 B2
O'Neil (45) Date of Patent: Mar. 17, 2026

(54) DOSAGE REGIME

(71) Applicant: NOVABIOTICS LIMITED, Aberdeenshire (GB)

(72) Inventor: Deborah O'Neil, Aberdeenshire (GB)

(73) Assignee: NOVABIOTICS LIMITED, Aberdeenshire (GB)

( * ) Notice: Subject to any disclaimer, the term of this patent is extended or adjusted under 35 U.S.C. 154(b) by 854 days.

(21) Appl. No.: 17/286,282

(22) PCT Filed: Oct. 17, 2019

(86) PCT No.: PCT/EP2019/078279
§ 371 (c)(1),
(2) Date: Apr. 16, 2021

(87) PCT Pub. No.: WO2020/079186
PCT Pub. Date: Apr. 23, 2020

(65) Prior Publication Data
US 2021/0386694 A1 Dec. 16, 2021

Related U.S. Application Data

(63) Continuation-in-part of application No. 16/163,407, filed on Oct. 17, 2018, now abandoned.

(30) Foreign Application Priority Data

Oct. 17, 2018 (CA) ................................ CA 3021344
Oct. 17, 2018 (EP) ..................................... 18201033

(51) Int. Cl.
*A61K 31/145* (2006.01)
*A61P 11/00* (2006.01)
*A61P 11/12* (2006.01)

(52) U.S. Cl.
CPC ............ *A61K 31/145* (2013.01); *A61P 11/00* (2018.01); *A61P 11/12* (2018.01)

(58) Field of Classification Search
CPC ......... A61K 31/145; A61P 11/00; A61P 11/12
See application file for complete search history.

(56) References Cited

U.S. PATENT DOCUMENTS

| | | | |
|---|---|---|---|
| 5,554,655 A | 9/1996 | Thoene | |
| 5,646,189 A | 7/1997 | Thoene | |
| 8,389,014 B2 | 3/2013 | Longo et al. | |
| 8,415,398 B2 | 4/2013 | Liang et al. | |
| 9,339,525 B2 * | 5/2016 | O'Neil .................. | A61K 31/145 |
| 9,364,491 B2 * | 6/2016 | O'Neil .................... | A61P 43/00 |
| 10,905,660 B2 * | 2/2021 | O'Neil .................. | A61K 45/06 |
| 11,369,568 B2 * | 6/2022 | O'Neil .................. | A61K 31/198 |
| 2011/0053894 A1 | 3/2011 | Walker et al. | |
| 2012/0129946 A1 | 5/2012 | Thoene | |
| 2012/0135969 A1 | 5/2012 | Weiler et al. | |
| 2014/0275279 A1 | 9/2014 | Eddy et al. | |
| 2016/0106689 A1 | 4/2016 | O'Neil | |
| 2016/0206575 A1 * | 7/2016 | O'Neil .............. | A61K 38/1729 |
| 2017/0081279 A1 | 3/2017 | Nguyen | |
| 2017/0348253 A1 | 12/2017 | O'Neil et al. | |
| 2019/0076368 A1 | 3/2019 | Gazzaniga et al. | |
| 2023/0338310 A1 | 10/2023 | O'Neil et al. | |

FOREIGN PATENT DOCUMENTS

| | | |
|---|---|---|
| CN | 105101955 A | 11/2015 |
| JP | 2014515356 A | 6/2014 |
| KR | 20140029372 A | 3/2014 |
| RU | 2013131391 A | 1/2015 |
| WO | 9013538 A1 | 11/1990 |
| WO | 2007062272 A1 | 5/2007 |
| WO | 2010091124 A2 | 8/2010 |
| WO | 2010/112848 A2 | 10/2010 |
| WO | 2010138419 A2 | 12/2010 |
| WO | 2012159103 A1 | 11/2012 |
| WO | 2013120086 A1 | 8/2013 |
| WO | 2016046523 A1 | 3/2016 |
| WO | 2016046524 A1 | 3/2016 |
| WO | 2016198842 A1 | 12/2016 |
| WO | 2017212239 A1 | 12/2017 |

OTHER PUBLICATIONS

Devereaux et al. "Cysteamine as a Future Intervention in Cystic Fibrosis Against Current and Emerging Pathogens: A Patient-based ex vivo Study Confirming its Antimicrobial and Mucoactive Potential in Sputum", 2015, EBioMedicine, 2, pp. 1507-1512 (Year: 2015).*
Procysbi, "Prescribing Information PROCYSBI", 2015, FDA.gov, pp. 1-19 (Year: 2015).*
Devereaux et al. "An Open-Label Investigation of the Pharmacokinetics and Tolerability of Oral Cysteamine in Adults with Cystic Fibrosis", 2016, Clinical Drug Investigation, 36, pp. 605-612 (Year: 2016).*
Devereaux et al. , "An open label investigation of the tolerability and pharmacokinetics of oral cysteamine in adults with cystic fibrosis", 2015, Journal of Cystic Fibrosis, Poster 141 (Year: 2015).*
"Cystagon", 2007, Mylan Pharmaceuticals, pp. 1-13 (Year: 2007).*
Jacquot et al. "Hyperinflammation in airways of cystic fibrosis patients: what's new?", 2008, Expert Review of Molecular Diagnostics, 8, pp. 359-363 (Year: 2008).*
Official Action dated Apr. 18, 2023 issued in corresponding European Patent Application No. 19786612.2.
European Search Report, dated Apr. 12, 2019, issued in corresponding European Patent Application No. 18201033.0.

(Continued)

*Primary Examiner* — Brenda L Coleman
*Assistant Examiner* — Madeline E Braun
(74) *Attorney, Agent, or Firm* — DLA Piper LLP (US)

(57) ABSTRACT

The present disclosure relates to use of cysteamine, formulations comprising cysteamine and pharmaceutically acceptable salts of cysteamine in the treatment of cystic fibrosis and conditions associated with cystic fibrosis.

11 Claims, 9 Drawing Sheets

(56) References Cited

OTHER PUBLICATIONS

International Search Report/Written Opinion, dated Jan. 9, 2020, issued in corresponding International Application No. PCT/EP2019/078279.

Anonymous: "NovaBiotics Announces New Data on Cysteamine (Nylexa (TM) as an Antimicrobial Resistance Breaker n Multi Drug Resistant Bacteria," Business Wire, Jun. 18, 2016, pp. 1-3.

Buchan B.E. "Formulation Studies on Cysteamine For The Treatment of Nephropathic Cystinosis" Aug. 1, 2011, [Retrieved on Sep. 6, 2017], pp. 1-223, XP55404192, Retrieved from the Internet: URL: https://core.ac.uk.download/pdf/1576960.pdf.

Buchan B.E. "The Formulation and Evaluation of a Dry Powder for Pulmonary Delivery in Cystinosis" Jan. 1, 2010, [Retrieved on Sep. 5, 2017], XP55403968, Retrieved from Internet: URL: https://www.cystinosis.org.uk/wp-content/uploads/2010/09/2010_RGU_Research Poster.pdf.

Cai et al. "Preparation, Characterization and Pulmonary Pharmacokinetics of a New Inhalable Zanamivir Dry Powder" Drug Delivery, Jun. 11, 2015, 23(6), pp. 1962-1971.

Charrier et al. "Cysteamine (Lynovex®), A Novel Mucoactive Antimicrobial & Antibiofilm Agent for the Treatment of Cystic Fibrosis" Orphanet Journal of Rare Diseases, Nov. 30, 2014, vol. 9(1):189 (11 pages).

Chinese Office Action for Chinese Patent Application No. 2017800353607, mailed Aug. 25, 2021, 30 pages (with English translation).

Chinese Third Office Action for Chinese Patent Application No. 201780035360.7, dated Jan. 30, 2022, 23 pages (with English Translation).

European Examination Report for European Patent Application No. 17735616.9 dated Dec. 16, 2020, 4 pages.

Examination Report for European Patent Application No. 21731565.4 dated Feb. 28, 2024, 5 pages.

Examination Report for Indian Patent Application No. 201817044232, dated Nov. 24, 2020, 6 pages.

Flume P.A et al. "Cystic Fibrosis Pulmonary Guidelines" American Journal of Respiratory and Critical Care Medicine, 2007, vol. 176, pp. 957-969.

Holbrook et al. "The Effect of Cysteamine and Epigallocatechin Gallate on the Inflammatory Phenotype in Cystic Fibrosis," Pediatric Pulmonology 32nd Annual North American Cystic Fibrosis Conference, Oct. 18-20, 2018, Denver, DO, published online Sep. 7, 2018, 3 pages.

International Search Report and Written Opinion for Application No. PCT/GB2017/051637, mailed on Sep. 15, 2017, 13 pages.

International Search Report and Written Opinion for Application PCT/GB2021/051269 dated Aug. 24, 2021 (17 pages).

Japanese Office Action for Japanese Patent Application No. 2018563831, mailed Apr. 19, 2022, 5 pages (with English translation).

Kandeel et al. "Virtual Screening and Repurposing of FDA Approved Drugs Against COVID-19 Main Protease," Life Sciences, Apr. 3, 2020, 251:1-5.

Keith R.L. "Lung Carcinoma" Merck Manual, 2019, Retrieved from the Internet: URL: https://www.merckmanuals.com/professional, 41 pages.

Khanna et al. "Binding of SARS-COV-2 Spike Protein to ACE2 is Disabled by Thiol-Based Drugs; Evidence from in / itro SARS-COV-2 Infection Studies," bioRxiv, Dec. 8, 2020, 1-22.

Komar. Application of Pantothenic Acid Drugs in the Treatment of Patients with Viral Hepatitis, vol. 63, No. 11, pp. 58-60 (1991)—see English translated summary on p. 60.

Korean Office Action for Korean Patent Application No. 1020187035476, mailed Sep. 24, 2021, 19 pages (with translation).

Lechuga-Ballesteros D et al. "Trileucine Improves Aerosol Performance and Stability of Spray-Dried Powders for Inhalation" Journal of Pharmaceutical Sciences, Jan. 2008, 97(1):287-302.

Li X et al. "Design, Characterization, and Aerosol Dispersion Performance Modeling of Advanced Spray-Dried Microparticulate/Nanoparticulate Mannitol Powders for Targeted Pulmonary Delivery as Dry Powder Inhalers" Journal of Aerosol Medicine and Pulmonary Drug Delivery, 2014, 27(2):81-93.

Lockhart S.P. "Inhaled Thiol and Phosphorothiol Radioprotectors Fail to Protect the Mouse Lung:, Radiotherapy and Oncology" Oct. 1, 1990, 19(2):187-191.

Mcintosh, "NovaBiotics Announces Fast-Track Repurposing of its Experimental Drug Nylexa for COVID-19 Trials and Plans for Earliest Possible Compassionate Use," Press Release, Apr. 13, 2020.

Mexico Office action for Mexican Application No. MX/a/2018/014278 dated Feb. 18, 2021, 7 pages (English Translation).

Russia Office Action for Russian Patent Application No. 2018142841, dated Feb. 20, 2021, 7 pages (English Translation).

Russia Office Action for Russian Patent Application No. 2018142841, dated Sep. 30, 2020, 15 pages (with English Translation).

United Kingdom Intellectual Property Office Search Report for Application No. GB2007768.1 dated Nov. 13, 2020 (5 pages).

Examination Report dated Jul. 17, 2024 issued in corresponding Australian Patent Application No. 2019360638 (4 pages).

Endeman et al., "Systemic cytokine response in patients with community-acquired pneumonia" 2011, European Respiratory Journal, vol. 37(6), pp. 1431-1438.

Ferrari et al., "Cysteamine re-establishes the clearance of Pseudomonas aeruginosa by macrophages bearing the cystic fibrosis-relevant F508del-CFTR mutation" 2017, Cell Death and Disease, vol. 8(e2544), pp. 1-11.

Karim et al., "An Association of Virus Infection with Type 2 Diabetes and Alzheimer's Disease" 2014, CNS & Neurological Disorders—Drug Targets, vol. 13, pp. 429-439.

Mcdonnell et al., "Zinc Ejection as a New Rationale for the Use of Cystamine and Related Disulfide-Containing Antiviral Agents in the Treatment of AIDS" 1997, Journal of Medicinal Chemistry, vol. 40(13), pp. 1969-1976.

Sadikot et al., "Pathogen-Host Interactions in Pseudomonas aeruginosa Pneumonia" 2005, American Journal of Respiratory and Critical Care Medicine, vol. 171, pp. 1209-1223.

Schnur, "Is COVID 19 Fueled by a Cytokine Storm", Apr. 8, 2020, NursingCenter, pp. 1-6, Retrieved Jul. 30, 2025, from Internet: URL: https://www.nursingcenter.Com/blogs-plus/blogs/blogs-post?identifier=Is-COVID-19-Fueled-by-a-Cytokine-Storm#/post/Is-COVID-19-Fueled-by-a-Cytokine-Storm.

Holbrook et al., "The effect of cysteamine and epigallocatechin gallate on the inflammatory phenotype in cystic fibrosis," Oct. 2018, Pediatric Pulmonology, 32nd Annual North American Cystic Fibrosis Conference, 3 pages. (Abstract).

Israeli Examination Report for Application No. 298267 dated Dec. 10, 2025, 4 pages.

* cited by examiner

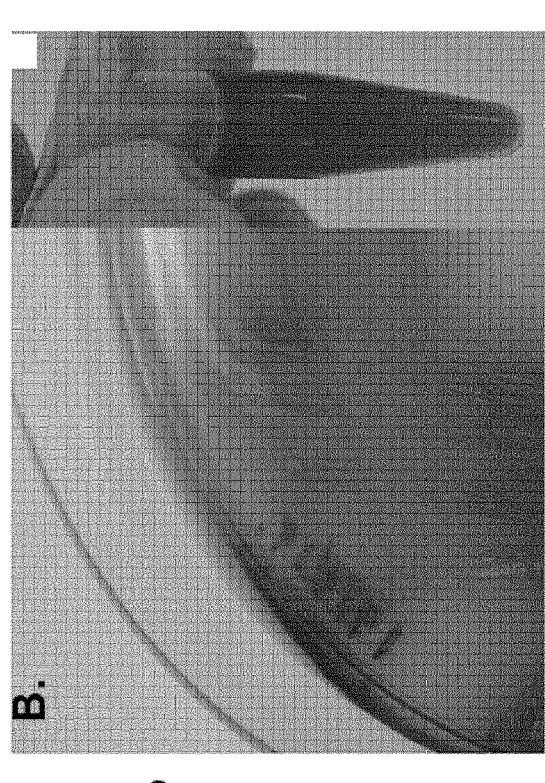
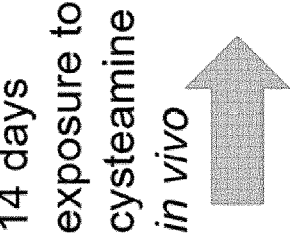
14 days exposure to cysteamine *in vivo*
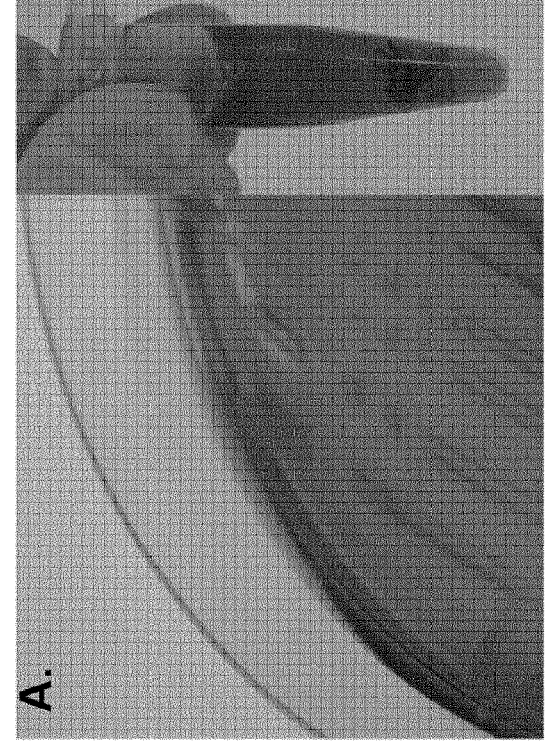
Fig 5. Alginate production showing efficacy of bi-daily dose

Figure 6

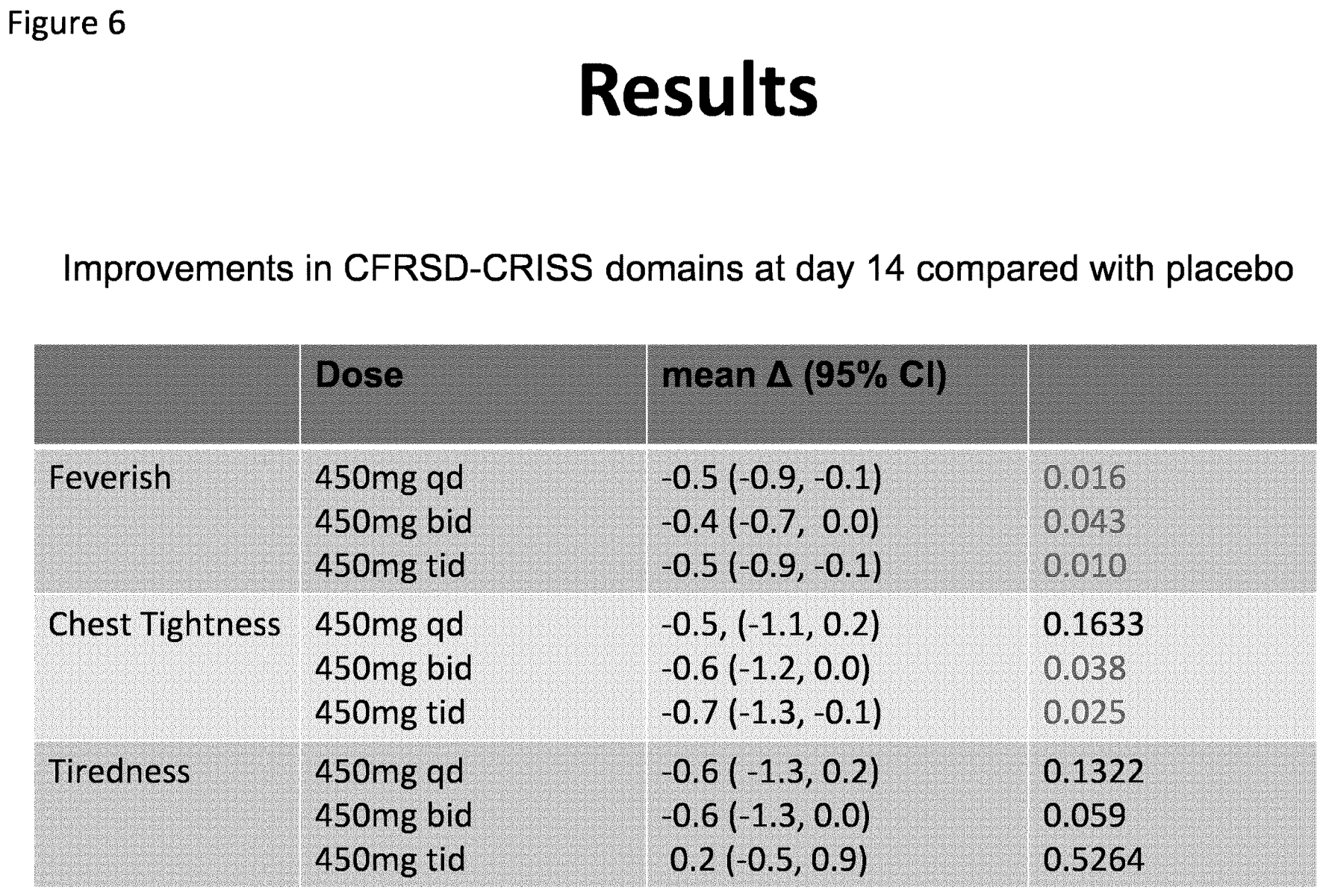

Results

Improvements in CFRSD-CRISS domains at day 14 compared with placebo

| Domain | Dose | mean Δ (95% CI) | |
|---|---|---|---|
| Feverish | 450mg qd | -0.5 (-0.9, -0.1) | 0.016 |
| | 450mg bid | -0.4 (-0.7, 0.0) | 0.043 |
| | 450mg tid | -0.5 (-0.9, -0.1) | 0.010 |
| Chest Tightness | 450mg qd | -0.5, (-1.1, 0.2) | 0.1633 |
| | 450mg bid | -0.6 (-1.2, 0.0) | 0.038 |
| | 450mg tid | -0.7 (-1.3, -0.1) | 0.025 |
| Tiredness | 450mg qd | -0.6 (-1.3, 0.2) | 0.1322 |
| | 450mg bid | -0.6 (-1.3, 0.0) | 0.059 |
| | 450mg tid | 0.2 (-0.5, 0.9) | 0.5264 |

DOSAGE REGIME

CLAIM OF PRIORITY

This application is a National Stage Application of PCT Application No. PCT/EP2019/078279 filed on Oct. 17, 2019 titled "Dosage Regime" which in turn claims priority to Application No. EP18201033.0 filed on Oct. 17, 2018, Application No. CA3021344 filed on October 17, and is a continuation in part of U.S. application Ser. No. 16/163,407 filed on Oct. 17, 2018, 2018, each of which is incorporated herein by reference in its entirety.

FIELD OF THE INVENTION

The present invention relates to use of cysteamine, formulations comprising cysteamine and pharmaceutically acceptable salts of cysteamine in the treatment of cystic fibrosis and conditions associated with cystic fibrosis.

BACKGROUND TO THE INVENTION

Cystic Fibrosis (CF) is the most common fatal inherited disease in Caucasian populations of European origin. In the UK, the carrier rate for this autosomal recessive condition is 1 in 25 and disease prevalence is approximately 1 in 2500. CF affects over 9000 people in the UK and about 70000 people globally (UK CF Registry, 2014). It is associated with reduced life expectancy, with the current median age of death at 26 to 29 years in the UK.

CF results from >1,000 mutations in the CF transmembrane regulator (CFTR) gene that codes for a chloride ion channel located in the apical membrane of epithelial cells; the CFTR has also been identified in non-epithelial cells. Although CF affects the pancreas, hepatobiliary tree and the intestinal and reproductive tracts, by far the most important aspect of the disease is respiratory, with 90% of the morbidity and mortality associated with CF resulting from chronic suppurative lung disease and ultimately respiratory failure (Goss, 2007).

CFTR mutations result in airway surface liquid dehydration, consequent impairment of mucocilliary clearance, bacterial colonisation of the airways and chronic suppurative lung disease. The chronic infection and inflammation of CF lung disease results in daily symptoms such as dyspnea, cough and sputum production. A characteristic feature of CF is intermittent episodes of acute worsening of symptoms, commonly known as exacerbations. Exacerbations are characterised by increased cough, increased sputum production, increased dyspnea, loss of appetite, weight loss and lung function decline (Goss, 2007). Such exacerbations have an adverse impact on patients' quality of life (Hegarty, 2009), incur significant healthcare costs (Britto, 2002) and are associated with a more rapid loss of lung function (Sanders, 2010; Sanders, 2011).

*Pseudomonas aeruginosa* is the most common pathogen in CF (UK CF Registry, 2014) and infection with this organism is characterised by persistence of the bacteria, repeated exacerbations and an accelerated rate of decline in lung function. Other Gram-negative bacteria can also infect or colonise the lung, probably the most clinically significant of which is the *Burkholderia cepacia* complex.

The Gram-negative bacteria that infect patients with CF are intrinsically resistant to many antibiotics and the prevalence of bacteria with newly acquired resistance has increased with improved life expectancy. Resistance rates in *P. aeruginosa* in the UK have increased dramatically with approximately 40% of patients resistant to two or more antibiotics in one study (Pitt, 2003). The development of antibiotic resistance in CF is most likely due to the intensive selective pressure provided by the large amounts of antibiotics used in these patients and the high frequency of hypermutatable *P. aeruginosa* found in CF lung infection (Oliver, 2000; Giwercman, 1990).

In CF, *P. aeruginosa* and the *B. cepacia* complex grow in biofilms and, as such, are much more resistant to antibiotics compared with planktonic-growing cells of the same isolate: minimum inhibitory concentration (MIC) and minimum bacterial concentration (MBC) can be 100- to 1000-fold greater in biofilms (Stewart, 2007). The issue of bacterial antibiotic resistance in CF is compounded by the relatively high incidence of adverse reactions (ARs) to antibiotics that have been reported in 9.5% of CF children and up to 25% in CF adults (Wills, 1998; Pleasants, 1994). The incidence of ARs increases with the number of courses of antibiotics administered (Koch, 1991).

The aggressive use of antibiotics to suppress chronic infection and to treat acute exacerbations is one of the mainstays of treatment in CF that has contributed to the increased survival of CF patients. However, the problems of multiple drug resistance and ARs are major clinical issues. This has led to calls for research into new antibiotics and new antibiotic strategies to target the biofilm and to increase the effectiveness of currently available antibiotics (Bats, 2011; Hoiby, 2002). Preclinical work indicates that cysteamine, a drug already licensed for another indication, has potentially beneficial actions on biofilms and micro-organisms, and was the basis for the current study.

Cysteamine is an amino thiol ($HSCH_2CH_2NH_2$) that is found endogenously in very low plasma levels as a consequence of coenzyme A metabolism (Besouw, 2013). Since 1976, cysteamine has been used to treat the lysosomal storage disorder, cystinosis. An immediate release formulation (Cystagon) was licensed for the treatment of cystinosis in the USA in 1994 and in the European Union (EU) in 1997. Adequate treatment of cystinosis with cysteamine reduces the rate of progression to end-stage renal failure, reduces extra renal manifestations and improves growth.

SUMMARY OF THE INVENTION

According to a first aspect there is provided cysteamine, a pharmaceutical formulation comprising cysteamine, or a pharmaceutically acceptable salt of cysteamine for use in a method of treating a lung disease, the method comprising administering to a patient in need thereof cysteamine bi-daily as two sub-doses, each sub-dose in the range of from 400 to 1000 mg, or in a single daily dose in the range of from 400-2000 mg.

The lung disease may be cystic fibrosis or condition associated with cystic fibrosis. For example, the condition could be a bacterial infection of the lung or a respiratory disease of the lung.

The treatment may be of pulmonary exacerbations in cystic fibrosis.

The total daily dose may be divided into equal sub-doses.

The total daily dose may be administered in equal divided sub-doses.

The total daily dose may be administered bi-daily as two sub-doses. When administered bi-daily, each dose may be administered 10 to 14 hours apart, or 11 to 13 hours apart. Each dose may be administered 12 hours apart.

Each sub-dose may comprise 400 to 1000 mg, 400 to 800 mg, 400 to 600 mg or 400 to 500 mg cysteamine. Each sub-dose may comprise 450 mg cysteamine.

The total daily dose may be in the range of from 400-2000 mg, 400-1400 mg, 450-1350 mg, 450-900 mg, 500-1800 mg, 600-1600 mg, 700-1400 mg, 800-1200 mg or 900-1000 mg, 800-2000 mg, 900-2000 mg. For example, the total daily dose may be 2000 mg, 1800 mg, 1600 mg, 1400 mg 1200 mg, 1000 mg or 900 mg, which may be administered bi-daily as two sub-doses of 1000 mg, 900 mg, 800 mg, 700 mg, 600 mg, 500 mg, or 450 mg each. The daily does is preferably less than 2000 mg.

Consequently, the daily does maybe 900 mg. The dose may be administered as two doses of 450 mg.

The cysteamine may be administered as an oral dose. For example, a liquid.

The oral dose may be a solid.

The salt may be cysteamine bitartrate.

The pharmaceutical formulation comprising cysteamine or a pharmaceutically acceptable salt thereof may further comprise one or more selected from the list: carriers, excipients, diluents, adjuvants and antimicrobial agents. Multiple of each member of the list is independently envisioned. The pharmaceutical formulation may consist essentially of cysteamine or a pharmaceutically acceptable salt thereof, optionally may further consist essentially of one or more selected from the list: carriers, excipients, diluents, adjuvants and antimicrobial agents.

In one embodiment the oral dose comprises 450 mg cysteamine or a pharmaceutically acceptable salt thereof.

In a second aspect there is provided a method of treating cystic fibrosis or a condition associated with cystic fibrosis comprising administering to a patient in need thereof a dose in the range 400-1000 mg once or bi-daily of cysteamine or a pharmaceutically acceptable salt thereof.

The disease treated by the method may be the same as that provide for in the first aspect of the present invention.

The method may be once daily.

The method may involve bi-daily administration of the dose. These dosages may be administered in equal divided sub-doses. The separation in time between sub-doses may be that provided for in the first aspect of the present invention. The sub-doses may be those descried for use with the first aspect of the present invention.

The method may involve the administration of a total daily dose in the range 800-1000 mg, or 400 to 2000 mg.

The total daily dose may be 900 mg. This may be administered as two sub-doses of 450 mg each.

The oral dose may be a solid dose. The oral dose may be a liquid.

The salt may be cysteamine bitartrate.

The cysteamine or a pharmaceutically acceptable salt thereof administered in the method may be any of the pharmaceutical formulations, or salt thereof described in the first aspect of the present invention.

The method may be conducted concomitantly with a further method of treating cystic fibrosis or a condition associated with cystic fibrosis.

The method may be an adjunct therapy.

Also described is cysteamine, a pharmaceutical formulation comprising cysteamine or a pharmaceutically acceptable salt of cysteamine for use in the treatment of cystic fibrosis or a condition associated with cystic fibrosis wherein the cysteamine is administered to a patient in need thereof in a total daily dose in the range 400-1400 mg. The total daily dose may be in the range 450-1350 mg. Also provided a method of treating cystic fibrosis or a condition associated with cystic fibrosis comprising administering to a patient in need thereof an oral dose comprising >300 mg cysteamine or a pharmaceutically acceptable salt thereof. The total daily dose may be in the range 450-900 mg. Each sub-dose may comprise >300 mg cysteamine.

Any features of the first and second aspect of the present invention may be combined with that of the third.

BRIEF DESCRIPTION OF THE DRAWINGS

The present invention will now be described by way of example only with reference to the accompanying Figures in which:

FIG. 5 shows: Alginate production from sputum after bi-daily dose at 450 mg of cysteamine. This figure shows alginate production after 120 h growth in Müller Hinton broth (MHB) at 37° C. by clonally-related, pyomelanin-producing, strains of *P. aeruginosa* isolated from sputum from a CF patient on (A) day 0, and (B) day 14 of the CARE-CF-1 trial taking 450 mg BID cysteamine. Isolate A produced 19.93 µg/ml (+/−1.9 SD) alginate and had mucoid phenotype. Isolate B produced 4.47 µg/ml (+/−2.39 SD) with dry colonies.

FIG. 6 shows: improvements in CFRSD-CRISS domains. Again, the best improvements were seen with a dose of 450 mg bi-daily.

DETAILED DESCRIPTION

Figure 1:
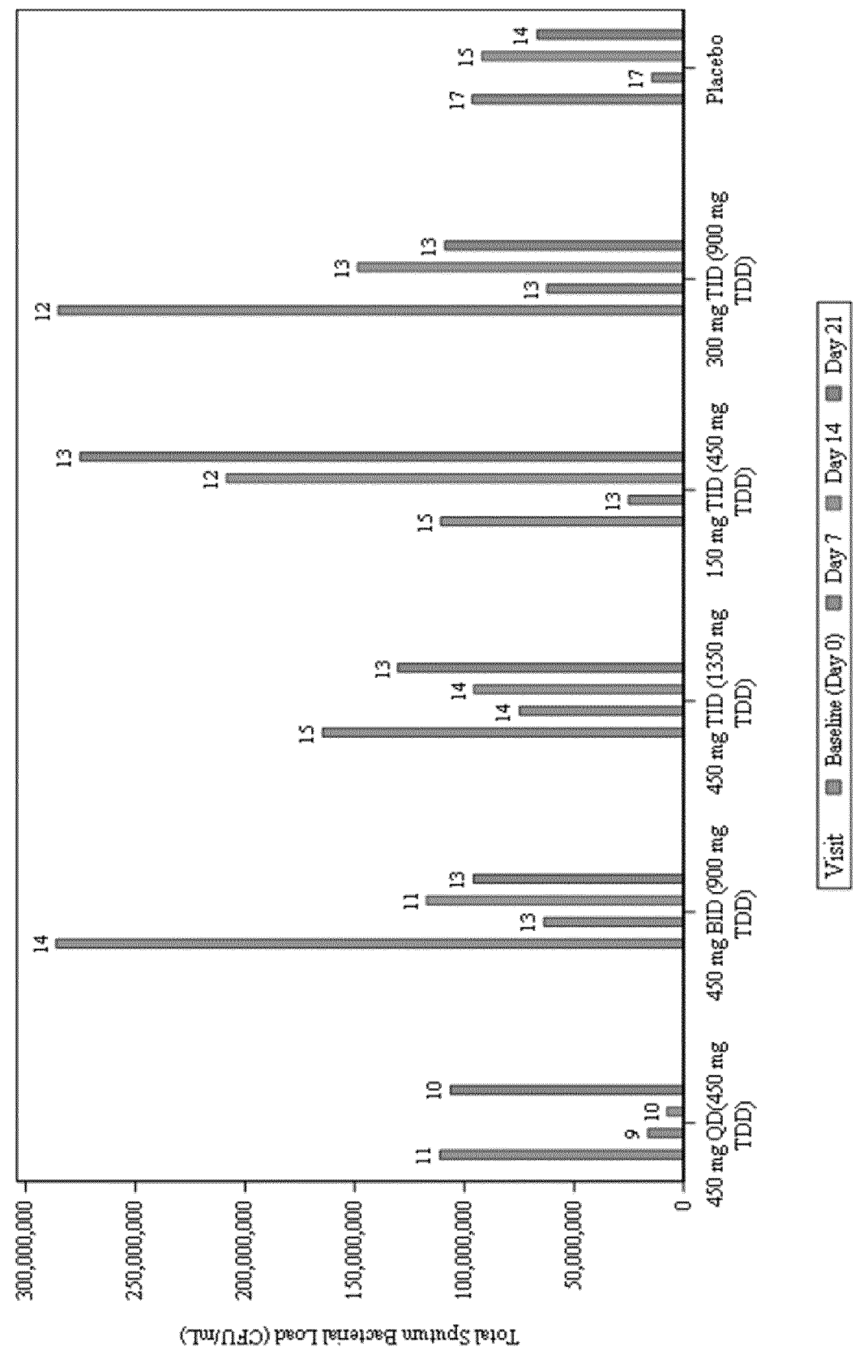
FIG. 1 shows: Total Sputum Bacterial Load Counts (CFU/mL) by Visit (ITT Population): BID=two times daily; CFU=colony forming units; ITT=Intent-to-Treat; MRSA=methicillin-resistant *Staphylococcus aureus*; QD=once daily; TDD=total daily dose; TID=three times daily. Note: Total sputum bacterial load is the total count of Gram-negative organisms and MRSA organisms isolated.

The present invention provides cysteamine, a pharmaceutical formulation comprising cysteamine or a pharmaceutically acceptable salt of cysteamine for use in treatment of a lung disease such as cystic fibrosis or a condition associated with cystic fibrosis.

The term "pharmaceutical formulation comprising cysteamine" encompasses the use of cysteamine optionally in combination with other undefined ingredients. The term "comprising" where used may optionally be substituted with "consisting essentially of" or "consisting".

As employed herein "cystic fibrosis" refers to the genetic disorder (described above) that affects mostly the lungs, but also the pancreas, liver, kidneys, and intestine.

Condition associated with cystic fibrosis as employed here refers to lung infections and other symptoms of cystic fibrosis that are related to cystic fibrosis but are not a result of the genetic disorder per se. Such conditions include, but are not limited to, growth failure due to malabsorption, vitamin deficiencies, hepatic steatosis, portal hypertension, biliary cirrhosis, neonatal obstructive jaundice, cholelithiasis, hypertrophic osteoarthropathy, arthritis, osteoporosis, meconium ileus, meconium peritonitis, intussusception, *volvulus*, fibrosing colonopathy, appendicitis, intestinal atresia, distal intestinal obstruction syndrome, inguinal hernia, bronchiectasis, bronchitis, bronchiolitis, pneumonia, atelectasis, haemoptysis, pneumothorax, reactive airway disease, cor pulmonale, respiratory failure, mucoid impaction of the bronchi, allergic bronchopulmonary aspergillosis, right ventricular hypertrophy, pulmonary artery dilation, hypersplenism, gastroesophageal reflux disease, pancreatitis, insulin deficiency, symptomatic hyperglycaemia, diabetes, infertility, amenorrhoea, or any combination thereof.

Lung diseases to be treated include but are not limited to: cystic fibrosis (CF), asthma, acute respiratory distress syndrome, chronic obstructive pulmonary disease (COPD), acute and chronic bacterial lung infection, acute lung injury, emphysema, bronchiectasis including non-CF bronchiectasis, influenza or any combination thereof.

Cysteamine can treat lung diseases which have a bacterial infection component as a result of its antimicrobial (including antibiotic, anti-biofilm, antibiotic potentiating and anti-virulence effects).

Cysteamine can also treat obstructive respiratory diseases as a result of its mucolytic and/or anti-inflammatory properties.

Cysteamine is a stable aminothiol which is biosynthesised in mammals during the breakdown of coenzyme A and has the chemical formula $C_2H_7NS$ ($HSCH_2CH_2NH_2$). Cysteamine has a direct antimicrobial effect, potentiates other antibiotics (quinolones and aminoglycosides, for example), is a potent mucolytic, disrupts biofilms inhibits bacterial virulence and is anti-inflammatory. Cysteamine as employed herein is intended to encompass pharmaceutically acceptable salts thereof.

Thus, without wishing to be bound by theory, the present inventors believe that cysteamine when administered according to the present invention functions in the patient by one of more mechanisms selected from the list: as an antimicrobial, in synergy with an additional antimicrobial agent, as a mucolytic and as a disruptor of biofilms.

Pharmaceutical formulation comprising cysteamine refers to any suitably formulated pharmaceutical comprising the requisite amount of cysteamine or a pharmaceutically acceptable salt thereof.

Total daily dose as employed herein refers to the dose given in total of the active ingredient over a 24-hour period.

In one embodiment cysteamine or a pharmaceutically acceptable salt thereof is administered to a patient in need thereof in a total daily dose in the range 400-1400 mg. For example, 425, 425, 475, 500, 550, 600, 650, 700, 750, 800, 850, 900, 950, 1000, 1050, 1100, 1150, 1200, 1250, 1300 or 1350 mg. Such as 450-1350 mg or 450-900 mg.

In one embodiment the total daily dose is administered in equal divided sub-dose. For example, two or three or more sub-doses. Such as two sub-doses.

Sub-dose as employed herein refers to a portion of the total daily dose. Sub-doses may be equally divided or unequally.

Typically, sub-doses are administered at different time points such as approximately 1, 2, 3, 4, 5, 6, 7, 8, 9, 10, 11 or 12 hours apart during a day. For example, a first sub-dose is administered at one time point then a second sub-dose is administered 4 to 12 hours later. Where a third sub-dose is administered, the second sub-dose is administered 4 to 6 hours later and the third sub-dose 4 to 6 hours after the second.

In one embodiment the total daily dose is administered bi-daily as two sub-doses.

Twice daily or bi-daily as used herein are equivalent and are intended to refer to where the total daily dose is divided and administered at two separate time points during the day.

In one embodiment the twice daily or bi-daily dose is administered at two separate time points during the day, such as approximately 1, 2, 3, 4, 5, 6, 7, 8, 9, 10, 11 or 12 hours apart. For example, the first dose is administered at one time point and the second dose is administered at a time point approximately 12 hours later.

In one embodiment each sub-dose comprises >300 mg cysteamine or a pharmaceutically acceptable salt thereof. For example, approximately: 310, 320, 330, 340, 350, 360, 370, 375, 380, 390, 400, 410, 420, 425, 430, 440, 450, 475, 500, 525, 550, 575, 600 mg or more. Such as approximately 400-600 mg, or 400 to 500 mg, for example 450 mg For example, the dose may be 400-600 mg bi-daily, i.e. 400-600 mg twice a day. For example, 450 mg twice a day. The second dose may be administered approximately 10-12 hours after the first dose.

Preferably, the treatment of the patient with the pharmaceutical formulations of the present invention begins with a bi-daily dose. That is, there is no previous scaling up of the treatment from a single dose to a bi-daily dose. The pharmaceutical formulations of the present invention are for use in treating the recited disorders as part of an isolate regimen. For example, the dose provided by the present invention is the first dose after diagnosis of an exacerbation, eg the bi-daily 450 mg dose is the first dose after diagnosis of an exacerbation.

As employed herein approximately refers to ±10% of the given value.

In one embodiment each sub-dose comprises at least 450 mg cysteamine or a pharmaceutically acceptable salt thereof. Such as 475, 500, 525, 550, 575, 600, 625, 650, 675, 700, 725, 750, 775, 800, 850, 900, 950 or 100 mg or more.

Typically, the total daily dose is administered to an adult human. Paediatric administration is anticipated to require loser total daily doses calculated on the equivalent dosage required to treat a given weight of the patient (for example, in kilograms). For example, 1 to 50 mg/kg. Further exemplary dosage ranges are discussed below.

Treatment as employed herein refers to prophylaxis of patients not currently experiencing an exacerbation as well treatment following diagnosis of an exacerbation. The term "treatment" relates to the effects of cysteamine in imparting a benefit to patients afflicted with cystic fibrosis or a condition associated with cystic fibrosis, including an improvement in the condition of the patient or delay in disease progression. The term exacerbation is a clinical term and means intermittent episodes of acute worsening of symptoms. Exacerbations are the most important clinical event clinicians deal with in CF patients. Exacerbations are characterised according to the European Consensus Group by a recent change in at least two of the following: increased cough, increased sputum production or change in colour; increased dyspnea, loss of appetite, weight loss and lung function decline (alternatively, using the Fuchs criteria, one can characterise a disorder as an exacerbation when it presents with 4 of the Fuch's criteria, eg any 4 of those symptoms listed above). These features have been used to define a pulmonary exacerbation in national treatment guidelines. Such exacerbations have an adverse impact on patients' quality of life, incur significant healthcare costs and are associated with a more rapid loss of lung function.

In one embodiment the cysteamine is administered as an oral dose. Oral dose includes an oral formulation.

An oral formulation or oral dose is one which is provided in a form suitable for oral delivery, for example a solution, suspension or a solid dose for example dry granules, a tablet, capsule, caplet, sublingual or buccal formulation. In one embodiment the formulation according to the present disclosure or employed in the present method is a solid dose formulation, for example provided as a unit.

In one embodiment the oral dose is a liquid.

Unit dose as employed herein refers to a discrete unit, for example a tablet, capsule, sachet, ampule or the like that contains one dose of the medicament.

In one embodiment the oral dose is a solid.

Solid dose formulations may comprise pharmaceutically acceptable excipients include those independently selected from microcrystalline cellulose, lactose, sodium citrate, calcium carbonate, calcium sulphate, dibasic calcium phosphate and glycine, mannitol, pregelatinised starch, corn starch, potato starch, disintegrants such as sodium starch glycollate, croscarmellose sodium and certain complex silicates, and granulation binders such as polyvinylpyrrolidone, talc and lubricants such as magnesium stearate, stearic acid.

Capsules may be filled with a powder or microgranules (of medicament alone or as blend with selected filler(s)) or alternatively a liquid, each comprising cysteamine and a carrier/carriers. Alternatively, capsulation may not be required and the powder or microgranules maybe delivered in a free-flowing form. This enables sprinkling of the powder or microgranules directly into the mouth or onto food. When in free-flowing form, the powder or microgranules may be provide in sachets which may form the unit doses of the present invention.

In one embodiment the solid dose formulation is a tablet or capsule.

In one embodiment the formulation is an immediate release tablet or capsule.

Immediate release and instant release are used interchangeably as employed herein.

Immediate-release formulation as employed herein refers to where substantially all of the cysteamine is released within a small period of time, for example 30 minutes or less.

In one embodiment the dosage form is an immediate release tablet or capsule containing approximately 450 mg of cysteamine per dosage form. Alternatively, multiple tablets or capsules containing a total equivalent amount of cysteamine may be employed. For example, 3 tablets or capsules each containing 150 mg cysteamine.

The formulation employed in the use of the invention may be administered in the form of a pharmaceutically acceptable salt. The pharmaceutically acceptable salts can be synthesised from cysteamine by conventional chemical methods. Generally, such salts can be prepared by reacting the free acid or base forms of cysteamine with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., US, 1985, p. 1418, the disclosure of which is hereby incorporated by reference; see also Stahl et al, Eds, "Handbook of Pharmaceutical Salts Properties Selection and Use", Verlag Helvetica Chimica Acta and Wiley-VCH, 2002.

The invention thus includes pharmaceutically-acceptable salts of the formulation employed in the use of the invention wherein the parent compound is modified by making acid or base salts thereof for example the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glutamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

In one embodiment the pharmaceutically acceptable salt is cysteamine bitartrate.

The invention includes prodrugs for the active pharmaceutical species of cysteamine, for example in which one or more functional groups are protected or derivatised but can be converted in vivo to the functional group, as in the case of protected amines, to the free amino group. The term "prodrug," as used herein, represents in particular structures which are rapidly transformed in vivo to the parent structure, for example, by hydrolysis in blood. The pro-drug may be cystamine.

In one embodiment the pharmaceutical formulation comprising cysteamine for use according to the invention further comprises one or more selected from the list: carriers, excipients, diluents, adjuvants and antimicrobial agents.

The composition may also include a pharmaceutically acceptable carrier, excipient or diluent. The phrase "pharmaceutically acceptable" is employed herein to refer to those compounds, materials, compositions, and/or dosage forms which are, within the scope of sound medical judgment, suitable for use in contact with the tissues of human beings or, as the case may be, an animal without excessive toxicity, irritation, allergic response, or other problem or complication, commensurate with a reasonable benefit/risk ratio.

To achieve the desired effect(s), cysteamine or the formulation comprising cysteamine may be administered as single or divided dosages, for example, of at least about 1 mg/kg to about 50 mg/kg, of at least about 2 mg/kg to about 40 mg/kg, at least about 3 mg/kg to about 30 mg/kg or at least about 4 mg/kg to about 20 mg/kg of body weight or at least about 5 mg/kg to about 15 mg/kg of body weight, although other dosages may provide beneficial results. The amount administered will vary depending on various factors including, but not limited to, the disease, the weight, the physical condition, the health, the age of the mammal, whether prevention or treatment is to be achieved, and if cysteamine is chemically modified.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the peptides of the invention may be essentially continuous over a pre-selected period of time or may be in a series of spaced doses.

To prepare the formulation, cysteamine is synthesised or otherwise obtained, purified as necessary or desired, and then lyophilised and stabilised. The formulation can then be adjusted to the appropriate concentration and optionally combined with other agents.

Thus, one or more suitable unit dosage forms comprising the therapeutic formulation of the invention can be administered by oral routes. Cysteamine may also be formulated in a lipid formulation or for sustained release (for example, using microencapsulation, see WO 94/07529, and U.S. Pat. No. 4,962,091). The formulations may, where appropriate, be conveniently presented in discrete unit dosage forms and may be prepared by any of the methods well-known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic formulations of the invention are prepared for oral administration, they are generally combined with a pharmaceutically acceptable carrier, diluent or excipient to form a pharmaceutical formulation, or unit dosage form. For oral administration, cysteamine may be present as a powder, a granular formation, a solution, a suspension, an emulsion or in a natural or synthetic polymer or resin for ingestion of the active ingredients from a chewing gum. The active ingredients may also be presented as a bolus, electuary or paste. Orally administered therapeutic compositions of the invention can also be formulated for sustained release, e.g., cysteamine can be coated, micro-encapsulated, or otherwise placed within a sustained delivery device. The total active ingredients in such formulations comprise from 0.1% to 99.9% by weight of the formulation.

Pharmaceutical formulations containing the therapeutic formulation of the invention can be prepared by procedures known in the art using well-known and readily available ingredients. For example, cysteamine can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatine, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites and the like.

For example, tablets or caplets containing the cysteamine can include buffering agents such as calcium carbonate, magnesium oxide and magnesium carbonate. Suitable buffering agents may also include acetic acid in a salt, citric acid in a salt, boric acid in a salt and phosphoric acid in a salt. Caplets and tablets can also include inactive ingredients such as cellulose, pregelatinised starch, silicon dioxide, hydroxyl propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatine capsules containing at least one peptide of the invention can contain inactive ingredients such as gelatine, microcrystalline cellulose, sodium lauryl sulphate, starch, talc, and titanium dioxide, and the like, as well as liquid vehicles such as polyethylene glycols (PEGs) and vegetable oil. Moreover, enteric-coated caplets or tablets containing cysteamine are designed to resist disintegration in the stomach and dissolve in the more neutral to alkaline environment of the duodenum.

The therapeutic formulation of the invention can also be formulated as elixirs or solutions for convenient oral administration. The pharmaceutical formulations of the invention can also take the form of an aqueous or anhydrous solution or dispersion, or alternatively the form of an emulsion or suspension or salve.

It is expected that the disclosed use of cysteamine, formulations and salts thereof will be administered concomitantly with additional or further treatments or therapies (including prophylactic uses). For example, concomitantly with cystic fibrosis treatments such as antimicrobial, anti-inflammatory, mucolytic, steroidal, bronchodilatory, enzyme supplements, vitamins, minerals, beta-2 adrenoreceptor antagonists, proton pump inhibitors, disease modifying therapy including genetic therapy and CFTR modulators. Alternatively, or additionally, concomitantly with treatments of any one or combination of the diseases described above.

As employed herein concomitantly means close to in time but not necessarily at the same time. For example, approximately 5-30, 10-30 minutes apart. For example, approximately, 5, 10 or 30 minutes apart, or more, such as approximately 60, 90, 120, 150, 180, 210, 240, 270, 300, 330, 360 minutes apart or more such as approximately 7, 8, 9, 10, 11 or 12 hours apart.

In one embodiment the use disclosed is as an adjunct therapy.

In one embodiment the sole active ingredient is cysteamine or a pharmaceutically acceptable salt thereof.

Also contemplated are combination products that include cysteamine and one or more other antimicrobial or antifungal agents, for example, polyenes such as amphotericin B, amphotericin B lipid complex (ABCD), liposomal amphotericin B (L-AMB), and liposomal nystatin, azoles and triazoles such as voriconazole, fluconazole, ketoconazole, itraconazole, pozaconazole and the like; glucan synthase inhibitors such as caspofungin, micafungin (FK463), and V-echinocandin (LY303366); griseofulvin; allylamines such as terbinafine; flucytosine or other antifungal agents, including those described herein.

Additionally, the formulations may be formulated as sustained release dosage forms and the like. The formulations can be so constituted that they release cysteamine, in a particular part of the intestinal or respiratory tract, possibly over a period of time. Coatings, envelopes, and protective matrices may be made, for example, from polymeric substances, such as polylactide-glycolates, liposomes, microemulsions, microparticles, nanoparticles, or waxes.

Specific non-limiting examples of the carriers and/or diluents that are useful in the pharmaceutical formulations of the present invention include water and physiologically acceptable buffered saline solutions such as phosphate buffered saline solutions pH 7.0-8.0.

The compositions of the present invention may further comprise an antimicrobial. The term "antimicrobial" is used to refer to agents that may be microbicidal and/or microbistatic. The antimicrobial agent may be antibacterial or antifungal.

"Antibacterial" or "antibiotic" is used to refer to antibacterial agents that may be derived from bacterial sources. Antibacterial agents may be bactericidal and/or bacteriostatic.

"Antifungal" is used to refer to antifungal agents that may be derived from bacterial sources. Antifungal agents may be fungicidal and/or fungistatic.

Generally, the antibiotic agent is of the group consisting of aminoglycosides, ansamycins, carbacephem, carbapenems, cephalosporins (including first, second, third, fourth and fifth generation cephalosporins), lincosamides, macrolides, monobactams, nitrofurans, quinolones, penicillin, sulfonamides, polypeptides and tetracyclins. Alternatively or additionally, the antibiotic agent may be effective against mycobacteria.

According to one embodiment, the antibiotic agent may be an aminoglycoside such as Amikacin, Gentamicin, Kanamycin, Neomycin, Netilmicin, Tobramycin or Paromomycin.

According to one embodiment, the antibiotic agent may be an ansamycin such as Geldanamycin and Herbimycin.

Alternatively, the antibiotic agent may be a carbacephem such as Loracarbef.

According to a further embodiment, the antibiotic agent is a carbapenem such as Ertapenem, Doripenem, Imipenem/Cilastatin or Meropenem.

Alternatively, the antibiotic agent may be a cephalosporin (first generation) such as Cefadroxil, Cefazolin, Cefalexin, Cefalotin or Cefalothin, or alternatively a Cephalosporins (second generation) such as Cefaclor, Cefamandole, Cefoxitin, Cefprozil or Cefuroxime. Alternatively, the antibiotic agent may be a Cephalosporins (third generation) such as Cefixime, Cefdinir, Cefditoren, Cefoperazone, Cefotaxime, Cefpodoxime, Ceftibuten, Ceftizoxime and Ceftriaxone or a Cephalosporins (fourth generation) such as Cefepime and Ceftobiprole.

The antibiotic agent may be a lincosamide such as Clindamycin and Azithromycin, or a macrolide such as Azithromycin, Clarithromycin, Dirithromycin, Erythromycin, Roxithromycin, Troleandomycin, Telithromycin and Spectinomycin.

Alternatively, the antibiotic agent may be a monobactam such as Aztreonam, or a nitrofuran such as Furazolidone or Nitrofurantoin.

The antibiotic agent may be a penicillin such as Amoxicillin, Ampicillin, Azlocillin, Carbenicillin, Cloxacillin, Dicloxacillin, Flucloxacillin, Mezlocillin, Nafcillin, Oxacillin, Penicillin G or V, Piperacillin, Temocillin and Ticarcillin.

The antibiotic agent may be a sulfonamide such as mafenide, sulfonamidochrysoidine, Sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxazole (Co-trimoxazole) (TMP-SMX).

The antibiotic agent may be a quinolone such as Ciprofloxacin, Enoxacin, Gatifloxacin, Levofloxacin, Lomefloxacin, Moxifloxacin, Nalidixic acid, Norfloxacin, Ofloxacin, Trovafloxacin, Grepafloxacin, Sparfloxacin and Temafloxacin.

Alternatively, the antibiotic agent may be a tetracycline such as Demeclocycline, Doxycycline, Minocycline and Oxytetracycline Alternatively or additionally, the antibiotic agent may be effective against mycobacteria.

In particular, the antibiotic agent may be Clofazimine, Lamprene, Dapsone, Capreomycin, Cycloserine, Ethambutol, Ethionamide, Isoniazid, Pyrazinamide, Rifampicin, Rifabutin, Rifapentine or Streptomycin.

The antibiotic agent may be a polypeptide such as Bacitracin, Colistin and Polymyxin B.

The antibiotic may be an antimicrobial peptide conforming to the following general structure of Formula (I) ((x)l (y)m)n, wherein l and m are integers from 1 to 10, for example 1 to 5; n is an integer from 1 to 10; X and Y, which may be the same or different, are independently a hydrophobic or cationic amino acid.

Preferably the first antimicrobial agent comprises amino acids according to the formula (I) wherein X and Y are cationic amino acids.

The antimicrobial peptide may comprise from 2 to 200 amino acids, for example 3, 4, 5, 6, or 7 up to 100 amino acids, including 3, 4, 5, 6, or 7 up to 10, 15, 20, 25, 30, 35, 40, 45 or 50 amino acids. According to one embodiment, the antimicrobial peptide comprises 3 or 4 to 50 amino acids. Alternatively the peptide may comprise more than 27 amino acids, typically 27 to 300 amino acids, suitably 27 to 200 amino acids.

The peptide may comprise 100 to 200 amino acids, 20 to 100, 20 and 45 amino acids such as 20, 25, 30, 35, 40, 42 or 45 amino acids. The peptide may comprise between 3 and 15 amino acids, for example 5 to 15 amino acids.

As used herein, the term "hydrophobic" refers to an amino acid having a side chain that is uncharged at physiological pH, that is not polar and that is generally repelled by aqueous solution.

As used herein, the term "cationic" refers to amino acids having a net charge that is greater than or equal to 0. Generally, the term "cationic" refers to amino acids having a net charge that is greater than zero.

Generally, a hydrophobic amino residue has a hydrophobicity greater than or equal to −1.10 and a charge greater than or equal to 0.

Hydrophobic amino acids may include, leucine phenylalanine, proline, alanine, tryptophan, valine, isoleucine and methionine.

Preferably X and/or Y are cationic amino acids for example selected from the group consisting of histidine, arginine and lysine. Preferably still X and/or Y are arginine or lysine. X and/or Y may be selected from non-naturally occurring amino acids for example the cationic amino acid ornithine.

X and/or Y may be optical isomers of a cationic amino acid as defined herein for example D or L-amino acids. Moreover, X and/or Y may be alternating amino acids.

The amino acids may be naturally occurring or synthetic. The invention also includes known isomers (structural, stereo-, conformational & configurational) and structural analogues of the above amino acids, and those modified either naturally (e.g. post-translational modification) or chemically, including, but not exclusively, phosphorylation, glycosylation, sulfonylation and/or hydroxylation.

The peptide may include one or more substitution of the cationic or hydrophobic amino acids X and Y. However, the peptide would predominantly comprise the cationic or hydrophobic amino acids X and Y. Typically the peptide may comprise 1 to 5 substitutions, suitably 1 to 3 substitutions, generally one substitution. The substitutions may be terminal or non-terminal.

The substitutions may consist of amino acids, or non-amino acids. The substitutions may be charged or uncharged. Typically, one or more of the substitutions are uncharged amino acids. Alternatively, or additionally one or more of the substitutions may be non-amino acids such as cysteamine.

Preferably X and Y are the same and are lysine or arginine.

The peptide may comprise predominantly arginine amino acids which may be substituted with one or more amino acids which are not arginine.

Generally, the peptide may comprise 7 to 20 arginine amino acids, optionally substituted with 1 to 5 non-arginine amino acids, typically 3 to 5 non-arginine substitutions.

Alternatively, the peptide may comprise 7 to 20 lysine amino acids, optionally substituted with 1 to 5 non-lysine amino acids, typically 3 to 5 non-lysine substitutions.

According to a further embodiment, the peptide may comprise 27 to 300 lysine amino acids, generally 27 to 200 lysine amino acids. Typically, the peptide comprises no nonterminal substitutions with non-lysine amino acids.

In the peptide of formula (I) 1 and m may be 1, 2, 3, 4, 5, 6, 7, 8, 9 or 10 and n may be 1, 2, 3, 4, 5, 6, 7, 8, 9 or 10.

In the peptide of formula (I) 1 may be 1, n may be 1 and m may be between 4 and 9, for example, m may be 3, 4, 5, 6, 7, 8 or 9.

In the peptide of formula (I) 1, n and/or m may be between 1 and 5, for example, 1, 2, 3, 4 or 5.

In the peptide of formula (I) 1 and m may be an integer between 0 and 7 and n may be an integer between 1 and 10.

In the peptide of formula (I) 1 and m may be 0, 1 or 2 and n may be an integer between 1 and 10.

In the peptide of formula (I) X and Y may be the same, 1 may be 0, m may be 1 and n may be 3, 4, 5, 6, 7, 8, 9 or 10.

In the peptide of formula (I) X and Y may be the same, 1 and m may be 1 and n may be 2, 3, 4 or 5. In the peptide of formula (I) X and Y may be the same, 1 may be 1, m may be 2 and n may be 1, 2, 3 or 4.

In the peptide of formula (I) X and Y may be the same, 1 and m may be 2 and n may be 1, 2, 3 or 4.

Preferably the first antimicrobial agent comprises a peptide sequence selected from the group consisting of polylysine and polyarginine.

In one embodiment, the first antimicrobial agent comprises a polylysine.

In an alternative embodiment, the first antimicrobial agent comprises polyarginine.

The peptide may be a glycopeptide. Examples of glycopeptides include vancomycin.

The antibiotic agent may be a lipopeptide. Examples of such lipopeptides include Daptomycin and Surfactin.

Generally, the antibiotic agent is active in the treatment or prophylaxis of infections caused by gram-negative or gram-positive bacteria, such as *Escherichia coli* and *Klebsiella*, particularly *Pseudomonas aeruginosa*.

The ratio of cysteamine to antibiotic in the products of the invention may be from 1:10 to 10:1; generally, at least 2:1 for example at least 3:1 or 4:1. According to a further embodiment the ratio may be approximately 1:1.

The antifungal may be selected from the group consisting of Fluconazole, Itraconazole, Caspofungin and Amphotericin B, for example, one or more of Fluconazole, Itraconazole and Caspofungin.

The active agents may be administered simultaneously, sequentially or separately. The active agents may be provided as a combination package. The combination package may contain the product of the invention together with instructions for simultaneous, separate or sequential administration of each of the active agents. For sequential administration, the active agents can be administered in any order.

In one embodiment there is provided a method of treating cystic fibrosis or a condition associated with cystic fibrosis comprising administering to a patient in need thereof an oral dose comprising >300 mg cysteamine. For example, 450 mg cysteamine.

In one embodiment the method is repeated bi-daily. For example, approximately 6 hours or more apart. For example, 7, 8, 9, 10, 11 or 12 hours apart. Such as 12 hours apart.

In one embodiment the method administers a total daily dose in the range 400-1400 mg. For example, approximately 425, 425, 475, 500, 550, 600, 650, 700, 750, 800, 850, 900, 950, 1000, 1050, 1100, 1150, 1200, 1250, 1300 or 1350 mg. Such as 450-1350 mg or 450-900 mg or 800-1000 mg. For example, the total daily dose is 900 mg.

In one embodiment the method employs an oral dose which is a solid dose.

In one embodiment the method is conducted concomitantly with a further method of treating cystic fibrosis or a condition associated with cystic fibrosis.

In one embodiment the method is an adjunct therapy.

Adjunct therapy (also known as adjuvant therapy, add-on therapy or adjuvant care) as employed herein means therapy that is given in addition to the primary or initial therapy to maximise its effectiveness or to improve patient outcomes.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

EXAMPLES

Example 1

Materials and Methods

A multicentre, double-blind, randomised, placebo-controlled, 6-arm trial of people with CF experiencing an acute exacerbation.

Inclusion Criteria:

CF lung disease, chronic infection with Gram-negative organism(s).

Age ≥3.8 years, weight >40 kg, FEV1>30% predicted in the prior 6 months.

Experiencing a new exacerbation, (≥4 symptoms Fuchs' criteria).

Intended treatment that included an aminoglycoside antibiotic.

Intervention:

Exacerbation treated as per standard of care

Randomised 1:1:1:1:1:1

Placebo three times a day 450 mg cysteamine once a day (qd) (total daily dose 450 mg)

150 mg cysteamine three times a day (tid) (total daily dose 450 mg)

450 mg cysteamine twice a day (bid) (total daily dose 900 mg)

300 mg cysteamine three times a day (tid) (total daily dose 900 mg)

450 mg cysteamine three times a day (tid) (total daily dose 1350 mg)

All participants took 3 tabs three times a day for 14 days

Sample Size:

Sample size n=120: with 20 in each of 6 groups 80% power to detect a 1.2 log reduction sputum bacterial load, with $\alpha=0.05$.

Outcomes:

Ascertained day 7, 14, 21 after randomisation 14 day course of study drug

Sputum bacterial load.

Patient Reported Outcome Measures (PROM)s

CF Respiratory Symptom Diary-Chronic Respiratory Infection Symptom Scale (CFRSD-CRISS)

Jarad and Sequeiros Symptom Score Questionnaire (JSSSQ)

CFQ-R

Sputum IL-8 and neutrophil elastase (NE) levels

FEV1% predicted

Blood leukocyte count (WCC)

Weight

CRP

AEs/ARs, SAEs/SARs

Results 89 participants randomised, 15 centres, USA, Italy, UK, in 16 months 89 patients randomised, 78 remained on medication for 14 days, Data available at day 14 for 81 (91%) participants

| Day 14 Sputum Microbiology (log10 Gram −ve organisms, CFU/ml) | | | | | | |
|---|---|---|---|---|---|---|
| | Placebo n = 15 | 450 mg qd n = 10 | 150 mg tid n = 12 | 450 mg bid n = 11 | 300 mg tid n = 13 | 450 mg tid n = 14 |
| D 0 mean (SD) | 6.67 (2.07) | 4.76 (3.66) | 6.43 (2.33) | 7.08 (2.50) | 7.21 (2.00) | 5.89 (2.61) |
| D 14 mean (SD) | 5.61 (2.80) | 4.49 (3.24) | 5.08 (3.87) | 6.25 (1.73) | 6.14 (2.48) | 6.27 (2.27) |
| D 14 Δbaseline mean (SD) | −1.38 (2.29) | 0.12 (2.04) | −1.24 (2.69) | −1.32 (2.30) | −0.98 (1.89) | 0.33 (2.27) |
| D 14 Δ −placebo mean (SD) | | 0.90 (0.97) | 0.03 (0.88) | 0.46 (0.91) | 0.87 (0.95) | 1.66 (0.86) |
| p value | | 0.36 | 0.97 | 0.61 | 0.36 | 0.059 |

| Day 21 (continued from day 14) | | | | | | |
|---|---|---|---|---|---|---|
| | Cysteamine 450 mg TDD | | Cysteamine 900 mg TDD | | Cysteamine 1350 mg TDD | |
| Visit | 450 mg QD (N = 11) | 150 mg TID (N = 15) | 450 mg BID (N = 15) | 300 mg TID (N = 16) | 450 mg TID (N = 15) | Placebo (N = 17) |
| Day 14 Change from Baseline (n) | 10 | 12 | 11 | 10 | 14 | 15 |
| Mean (SD) | 0.12 (2.045) | −1.24 (2.686) | −1.32 (2.298) | −0.98 (1.894) | 0.33 (2.270) | −1.38 (2.291) |
| Min, Max | −1.6, 5.4 | −7.7, 1.9 | −3.9, 3.1 | −4.4, 1.2 | −3.0, 5.1 | −6.0, 2.0 |
| LSMD (cysteamine − placebo) (SE) | 0.72 (0.94) | 0.03 (0.85) | 0.72 (0.88) | 0.82 (0.91) | 1.57 (0.82) | |
| 95% CI of LSMD | −1.15, 2.59 | −1.68, 1.73 | −1.03, 2.46 | −0.99, 2.63 | −0.07, 3.21 | |
| p-value[a] | 0.4445 | 0.9753 | 0.4165 | 0.3683 | 0.0602 | |
| LSMD (cysteamine QD/ BID − TID) (SE) | | 0.69 (0.97) | | −0.11 (0.97) | | |
| Day 21 Change from Baseline (n) | 10 | 13 | 12 | 10 | 13 | 14 |
| Mean (SD) | −1.22 (2.760) | −0.26 (1.639) | −1.04 (2.891) | −0.87 (1.677) | 0.93 (2.348) | −0.18 (1.238) |
| Min, Max | −6.8, 2.9 | −4.3, 1.4 | −8.7, 3.0 | −3.5, 1.6 | −2.2, 5.0 | −2.6, 2.1 |
| LSMD | −1.56 | 0.05 | −0.41 | −0.24 | 0.99 | |

-continued

| | | | | | |
|---|---|---|---|---|---|
| (cysteamine − placebo) (SE) | (0.88) | (0.79) | (0.80) | (0.86) | (0.79) |
| 95% CI of LSMD | −3.31, 0.19 | −1.53, 1.63 | −2.02, 1.19 | −1.95, 1.47 | −0.58, 2.55 |
| p-value[b] | 0.0799 | 0.9511 | 0.6117 | 0.7802 | 0.2130 |

BID = two times daily;
CFU = colony forming units;
CI = confidence interval;
ITT = Intent-to-Treat;
LSMD = least square mean difference;
MMRM = mixed model for repeated measures;
QD = once daily;
SD = standard deviation;
SE = standard error;
TDD = total daily dose;
TID = three times daily
Note:
Sputum samples with a total gram-negative bacterial load of 0 CFU/mL had the $\log_{10}$-transformed value computed as $\log_{10} (1) = 0$ and results above the limit of quantification set to the reported limit of quantification.
$^a$ = P-values, LSMD, and 95% CI were based on an MMRM model with an unstructured covariance matrix, factors for treatment group (6 levels: 450 mg QD, 150 mg TID, 450 mg BID, 300 mg TID, 450 mg TID, and placebo), visit (2 levels: Day 7 and Day 14), and visit by treatment group interaction and the baseline score as a continuous covariate. The Kenward and Roger method was used to calculate the denominator degrees of freedom.

Day 14 PROM (chronic respiratory
infection symptom scale - CRISS)
Significant improvements in PROM: Chronic
Respiratory Infection Symptom Scale (CFRSD-CRISS)

| | Placebo n = 17 | 450 mg qd n = 10 | 150 mg tid n = 13 | 450 mg bid n = 14 | 300 mg tid n = 13 | 450 mg tid n = 14 |
|---|---|---|---|---|---|---|
| D 0 mean (SD) | 48.5 (10.6) | 48.9 (12.1) | 47.5 (8.10) | 54.3 (13.1) | 51.0 (10.9) | 56.1 (8.82) |
| D 14 mean (SD) | 32.2 (14.2) | 26.1 (12.6) | 32.4 (13.3) | 25.4 (15.5) | 34.2 (15.0) | 31.6 (14.0) |
| D 14 Δbaseline mean (SD) | −16.3 (15.0) | −24.3 (16.3) | −15.5 (12.4) | −28.1 (16.8) | −14.8 (8.53) | −23.9 (16.4) |
| D 14 Δ −placebo mean (SD) | | −9.0 (5.24) | 0.8 (4.78) | −10.6 (4.94) | 1.9 (4.90) | −4.8 (4.99) |
| p value | | 0.090 | 0.87 | 0.035 | 0.70 | 0.34 |

Reduction in CRISS score with placebo = MCID,
Cysteamine 450 mg bid further 10 point reduction,
p = 0.035

Mean Change from Baseline in CRFSD-CRISS - Linear MMRM Model with Observed Data (ITT Population)

| Visit | Cysteamine 450 mg TDD | | Cysteamine 900 mg TDD | | Cysteamine 1350 mg TDD | |
|---|---|---|---|---|---|---|
| | 450 mg QD (N = 11) | 150 mg TID (N = 15) | 450 mg BID (N = 15) | 300 mg TID (N = 16) | 450 mg TID (N = 15) | Placebo (N = 17) |
| Baseline: Observed | 48.9 | 47.5 | 54.3 | 51.0 | 56.1 | 48.5 |
| Mean (SD) | (12.14) | (8.10) | (13.13) | (10.93) | (8.82) | (10.61) |
| Min, Max | 29, 68 | 29, 59 | 37, 91 | 34, 68 | 37, 70 | 29, 68 |
| Day 7 Change from Baseline (n) | 10 | 13 | 15 | 14 | 15 | 17 |
| Mean (SD) | −18.1 (10.19) | −11.9 (7.98) | −19.1 (10.65) | −10.5 (5.91) | −17.8 (12.67) | −16.4 (8.31) |
| Min, Max | −34, −3 | −27, −3 | −42, −8 | −20, 0 | −47, 0 | −32, 0 |
| LSMD | −1.10 | 4.25 | −0.78 | 6.48 | 1.11 | |
| (cysteamine − placebo) (SE) | (3.55) | (3.28) | (3.20) | (3.22) | (3.23) | |
| 95% CI of LSMD | −8.17, 5.97 | −2.28, 10.78 | −7.15, 5.59 | 0.08, 12.89 | −5.33, 7.55 | |
| p-value[a] | 0.7569 | 0.1991 | 0.8081 | 0.0474 | 0.7324 | |
| Day 14 Change from Baseline (n) | 10 | 13 | 14 | 13 | 14 | 17 |
| Mean (SD) | −24.3 (16.35) | −15.5 (12.48) | −28.1 (16.88) | −14.8 (8.53) | −23.9 (16.41) | −16.3 (15.00) |
| Min, Max | −63, −5 | −42, 0 | −56, −3 | −35, −3 | −56, −3 | −44, 16 |
| LSMD | −7.36 | 0.57 | −9.85 | 2.32 | −6.27 | |

-continued

| Mean Change from Baseline in CRFSD-CRISS - Linear MMRM Model with Observed Data (ITT Population) | | | | | | |
| --- | --- | --- | --- | --- | --- | --- |
| | Cysteamine 450 mg TDD | | Cysteamine 900 mg TDD | | Cysteamine 1350 mg TDD | |
| Visit | 450 mg QD (N = 11) | 150 mg TID (N = 15) | 450 mg BID (N = 15) | 300 mg TID (N = 16) | 450 mg TID (N = 15) | Placebo (N = 17) |
| (cysteamine – placebo) (SE) | (5.46) | (5.04) | (4.93) | (5.01) | (4.96) | |
| 95% CI of LSMD | −18.24, 3.51 | −9.47, 10.62 | −19.68, −0.02 | −7.65, 12.30 | −16.14, 3.60 | |
| p-value[a] | 0.1814 | 0.9098 | 0.0496 | 0.6439 | 0.2097 | |
| LSMD (cysteamineQD/ BID – TID) (SE) | | −7.94 (5.76) | | −12.17 (5.21) | | |
| 95% CI of LSMD | | −19.41, 3.54 | | −22.55, −1.79 | | |
| p-value[a] | | 0.1725 | | 0.0222 | | |

[2]= P-values, LSMD, and 95% CI were based on an MMRM model with an unstructured covariance matrix, factors for treatment group (6 levels: 450 mg QD, 150 mg TID, 450 mg BID, 300 mg TID, 450 mg TID, and placebo), visit (2 levels: Day 7 and Day 14), and visit by treatment group interaction and the baseline score as a continuous covariate. The Kenward and Roger method was used to calculate the denominator degrees of freedom.

20

| Day 14 Blood Leukocyte Count (×10$^9$/l) | | | | | | |
| --- | --- | --- | --- | --- | --- | --- |
| | Placebo n = 17 | 450 mg qd n = 10 | 150 mg tid n = 13 | 450 mg bid n = 14 | 300 mg tid n = 13 | 450 mg tid n = 14 |
| D 0 mean (SD) | 12.42 (4.19) | 10.71 (3.26) | 12.14 (3.92) | 10.68 (2.76) | 10.76 (3.40) | 13.53 (3.32) |
| D 14 mean (SD) | 10.47 (4.29) | 8.52 (2.97) | 9.71 (5.13) | 7.45 (2.06) | 10.55 (4.07) | 9.79 (2.53) |
| D 14 Δbaseline mean (SD) | −1.57 (4.71) | −2.22 (2.35) | −2.64 (3.91) | −3.41 (3.57) | −0.19 (3.83) | −4.06 (2.41) |
| D 14 Δ −placebo Mean (SD) | | −1.49 (1.20) | 0.00 (1.16) | −2.43 (1.11) | −0.24 (1.19) | −1.11 (1.13) |
| p value | | 0.22 | 1.00 | 0.033 | 0.84 | 0.33 |

Figure 2:
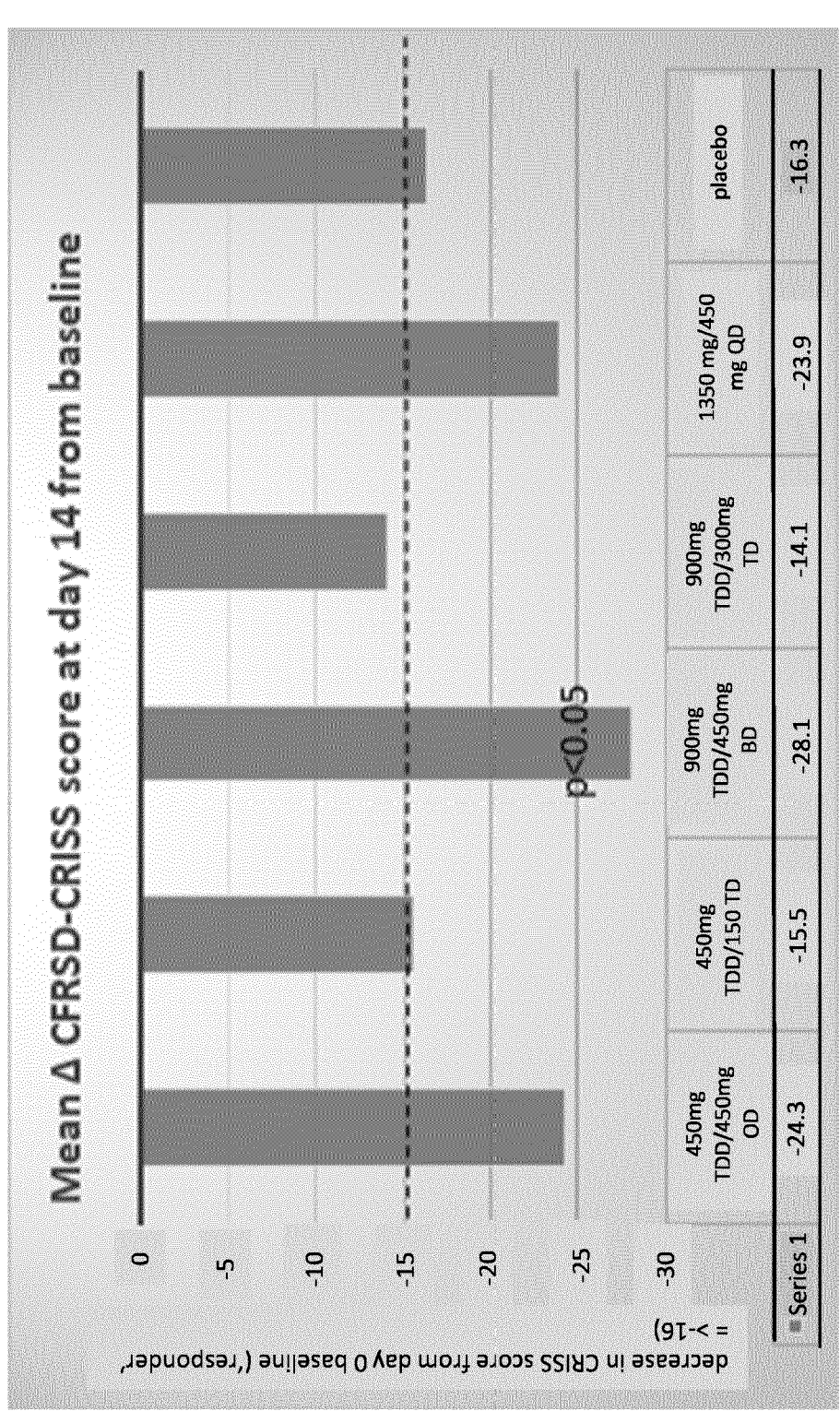
FIG. 2 shows: Mean $\Delta$ CFRSD-CRISS score at day 14 from baseline
Figure 3:
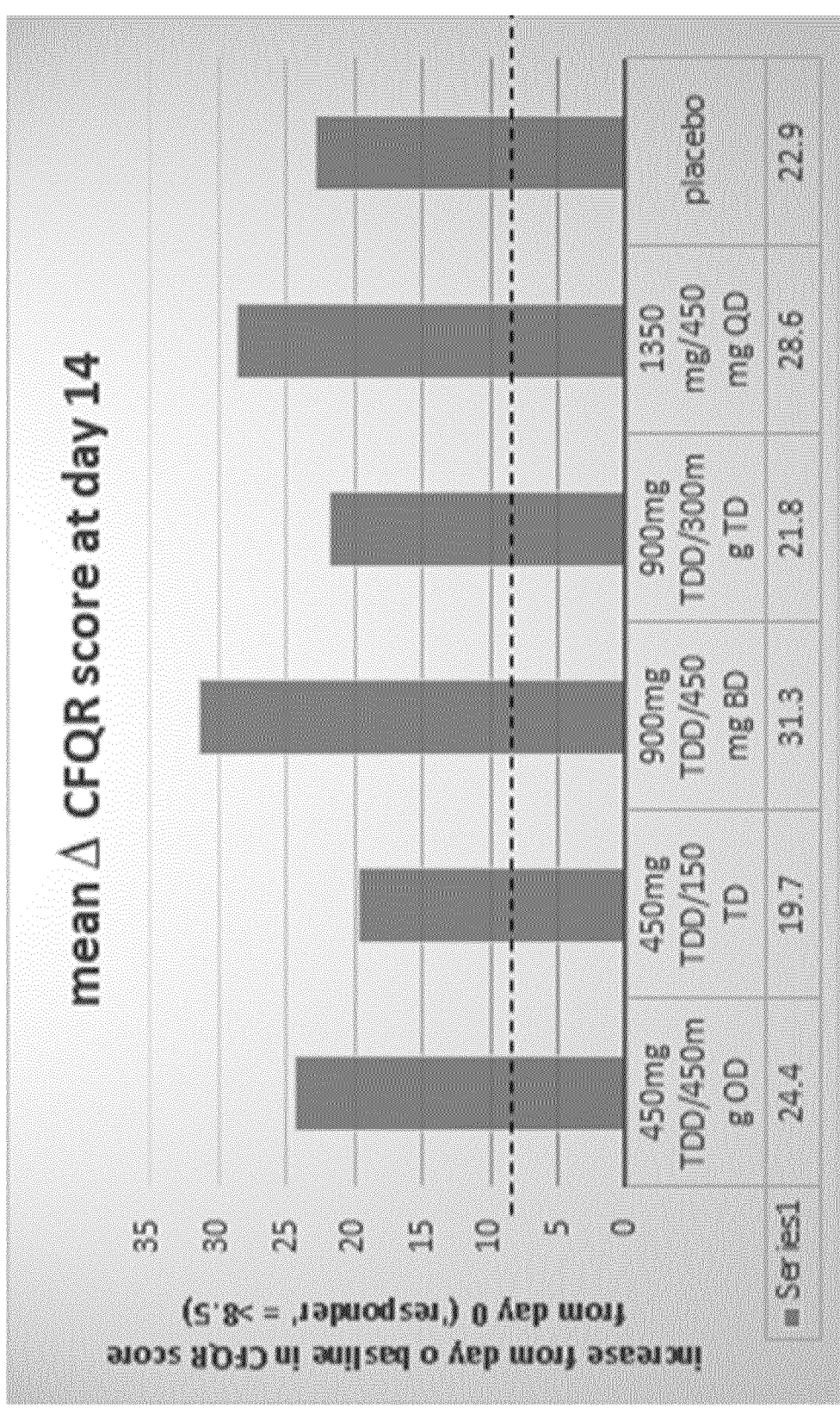
FIG. 3 shows: Mean $\Delta$ CFQR score at day 14
Figure 4:
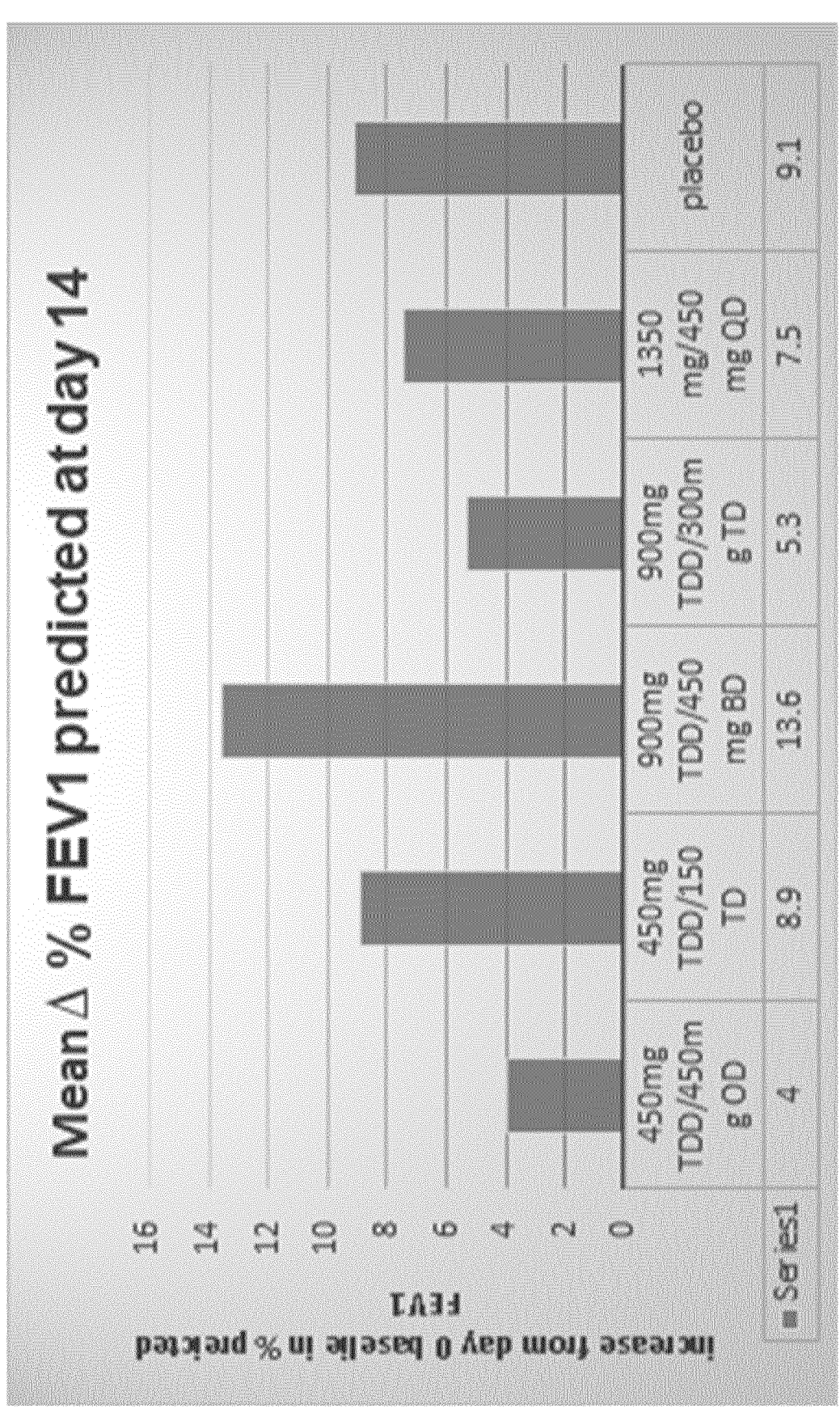
FIG. 4 shows: Mean $\Delta$ % FEV1 predicted at day 14

FIG. 1 illustrates the change in Gram negative bacterial load of patient sputum shown in the table above over time. FIG. 2 shows the significant reduction in CRISS score at day 14 compared with standard of care therapy plus placebo. It also shows how the clinical trial agrees with previously validated studies describing a −16-point reduction in CRISS score in response to standard of care therapy alone during acute pulmonary exacerbations of CF. 450 BID dose gave a significant improvement over and above placebo. There were also non-significant reductions in CRISS for other 450 doses. This patient reported outcome measure (PROM), which asks for a 24 hour recall of patients memory of symptoms, is best for evaluating clinical improvements in acute exacerbations. The CFQR PROM illustrated in FIG. 3 has a longer recall, but still showed non-significant improvements in the score above for 450 doses, greatest for 450 BID.

Example 2

FIG. 5 illustrates that non-mucoid strains can be selected for with standard of care therapy plus 450 BID dose of cysteamine.

Results provided in FIG. 5 were derived from a study that conforms to the general quantitative assay described in J. Phycol. 13, 345-348 (1977) "Alcian Blue: A Quantitative Aqueous Assay for Algal Acid and Sulfated Polysaccharides"; J Ramus.

Interestingly, as is seen form the results in FIG. 5, the production of alginate/extracellular polysaccharide in mucoid strains is also inhibited by exposure to cysteamine.

Example 2

Figure 8:
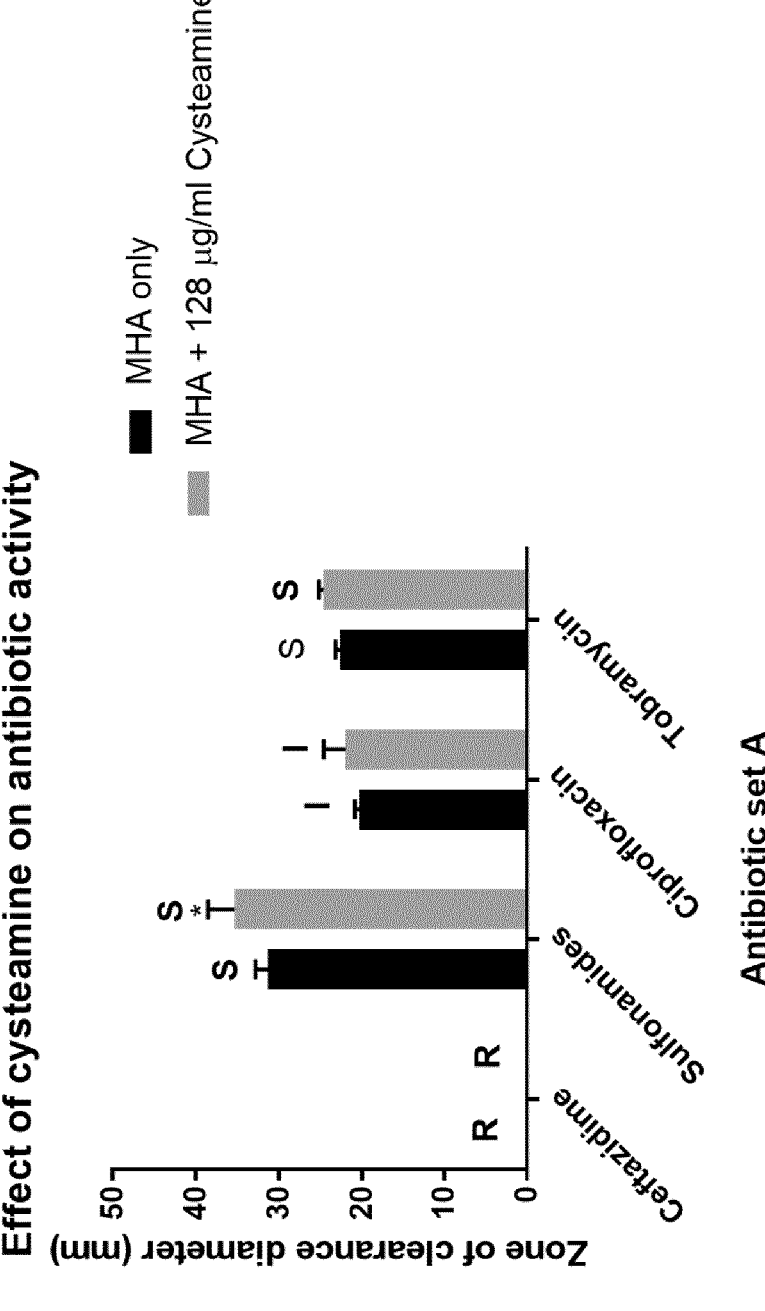
FIG. 8 shows: Effect of cysteamine on antibiotic activity against *P. aeruginosa* isolate. Legend: 5, I, R=sensitive, intermediate or resistant by interpretive criteria for antibiotic disc sensitivity testing method against *P. aeruginosa*. No criteria for sulphonamides against *P. aeruginosa*, however Bactrim/co-trimoxazole sometimes used in CF therefore included here with interpretive criteria for *Stenotrophomonas*. *=p<0.05 two-way ANOVA Sidak's multiple comparison test.

FIG. 8 illustrates the significant increase in zone of clearance and sensitivity to sulphonamides in a *P. aeruginosa* isolate from CF sputum determined using Kirby Bauer methods for antibiotic disc sensitivity determination (Hudzicki 2009, American Society for Microbiology) when grown on Müller Hinton agar containing cysteamine compared with agar alone.

Example 3

Patient trialled with combination treatment of 450 mg bi-daily in combination with antibiotics.

Figure 7:
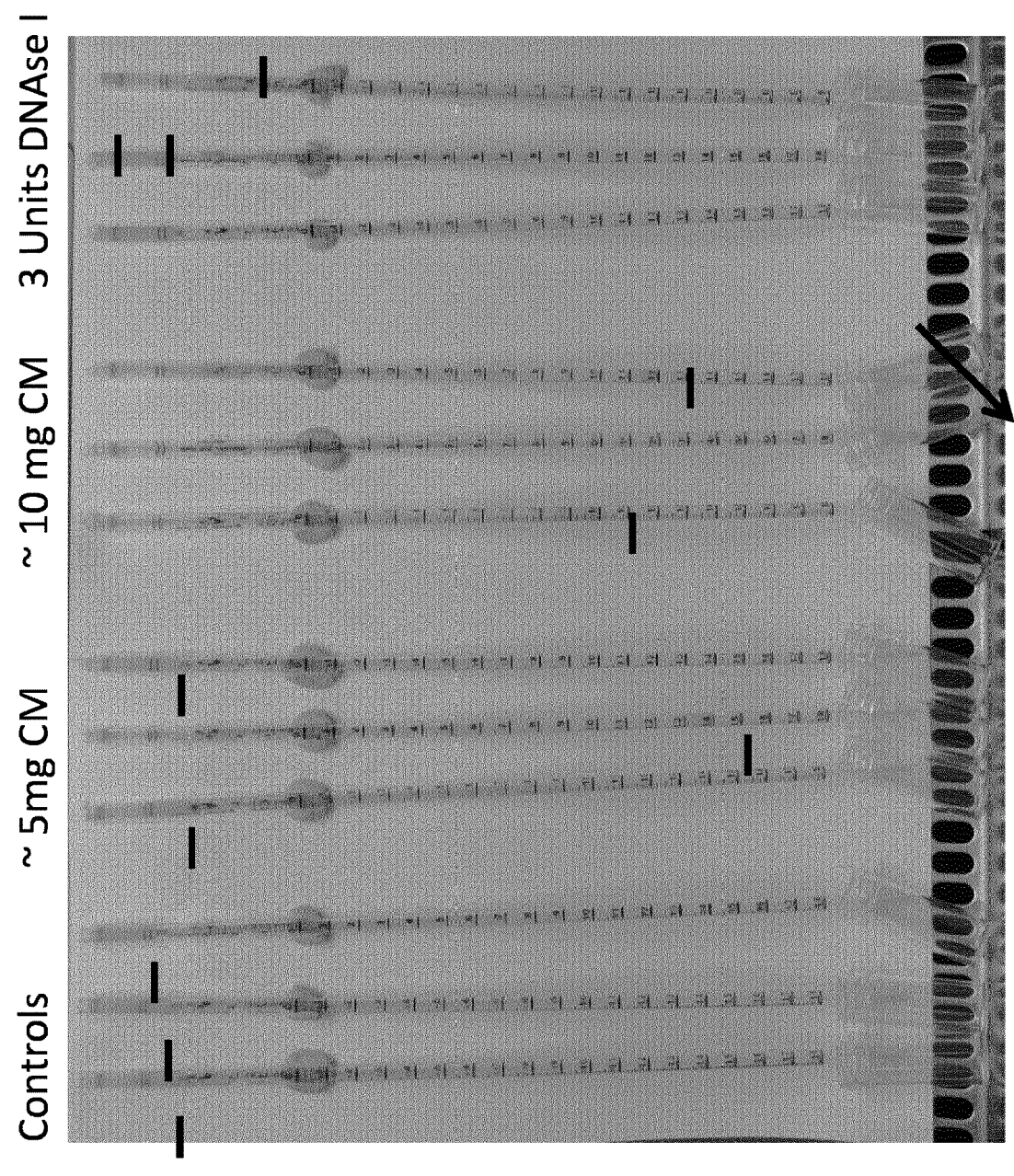
FIG. 7 shows: Mucolysis using cysteamine (5% w/w) formulation (CM).

Patient had very thick/purulent sputum. The sputum from this patient was responsive to 5% cysteamine DPI formulation. Addition of DNAse I (Pulmozyme) at physiological concentration is having no effect, but this patient is already on Pulmozyme and recently had the dose tripled. The patient's sputum responded to in vitro tests with cysteamine (see FIG. 7). The sputum response was conducted in accordance with the general method outlined in EBioMedicine 2 (2015) 1507-1512 "Cysteamine as a Future Intervention in Cystic Fibrosis Against Current and Emerging Pathogens: A Patient-based ex vivo Study Confirming its Antimicrobial and Mucoactive Potential in Sputum", Graham Devereux et al.

In vitro tests with cysteamine and various antibiotics showed increased sensitivity with the combination with various antibiotics and the 450 mg bi-daily dose of cysteamine (see FIG. 8). As a result, the patient was taken off regimen of ceftolozane+tazobactam, Colomycin and Pulmozyme and put onto 14-day course of cysteamine 450 mg BID (bi-daily) with Tobramycin and Colomycin. Patient was discharged from hospital 3-days later.

Example 4

Figure 9:
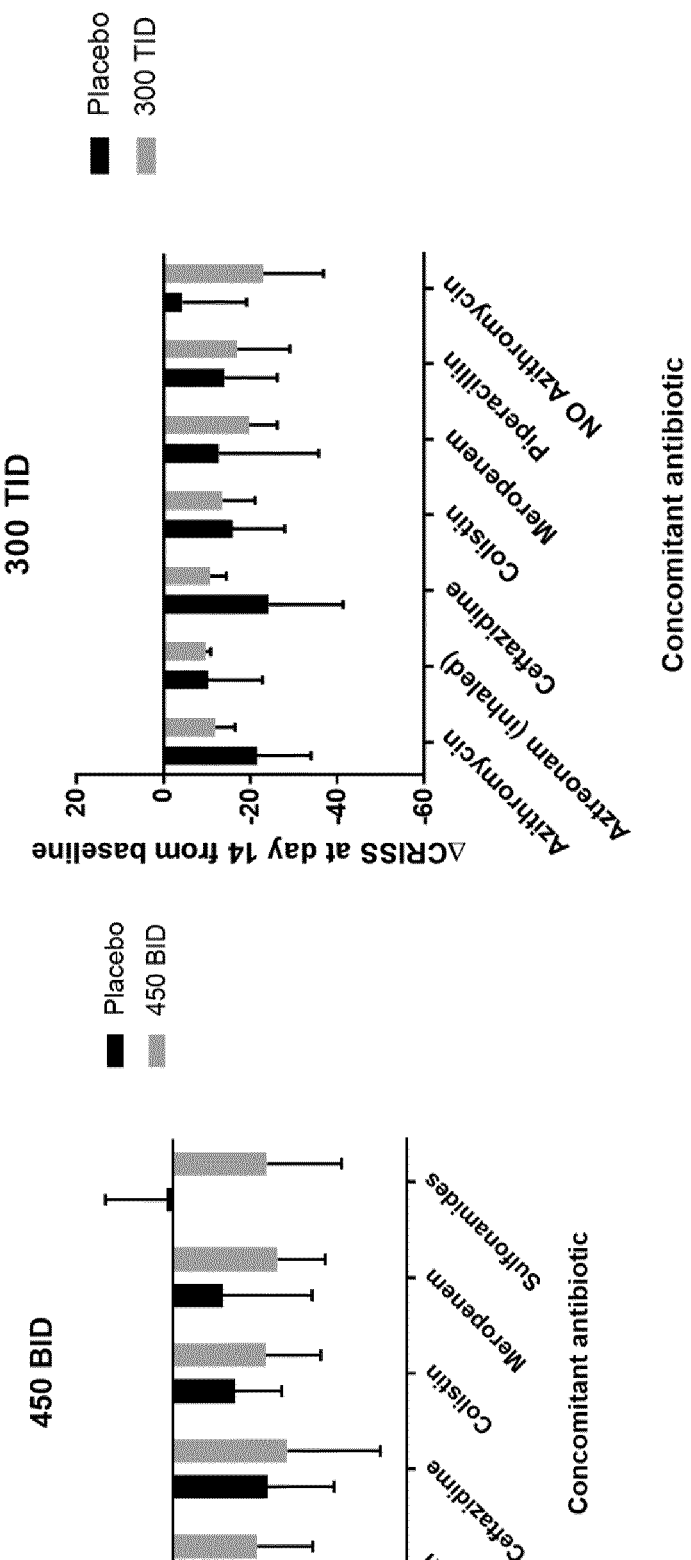
FIG. 9 shows: a comparison between 450 BID and 900 mg administered instead via 3 times 300 mg doses. The bi-daily dose potentiates other antibiotics more than the 300 mg three times a day dosage regime.

All patients on the CARE-CF-1 trial were on standard of care therapy for treatment of pulmonary exacerbation, however the antibiotic regime varies considerably across sites and between patients and as expected patients are often receiving multiple antibiotics as part of the standard of care. FIG. 9 is post-hoc analysis of trial data examining the impact on CRISS score for patients on 450 BID or 300 TID treatments with a selection of concomitant antibiotics (where number of per-protocol patients receiving this antibiotic on this dosage regime=n>3). This was conducted to examine if any specific combinations of cysteamine with antibiotics appear to be particularly beneficial or could be contraindicated in terms of the impact on CRISS. Across all cysteamine treatment regimens, those patients not receiving azithromycin did significantly better than placebo (though there was no detrimental effect of azithromycin co-therapy). This figure illustrates, as with other outcomes, that 450 dose regimen, including 450 BID showed non-significant improvements in CRISS across all antibiotics that were examined compared to placebo group. There were no antibiotic-specific significant reductions in CRISS for any dose regimen.

Discussion/Conclusions

Cysteamine has significant effects alone and used as an adjunct to treatment of exacerbations Optimal dose based on CRISS and WCC is 450 mg bid Supported by concordant trends on CFQ-R, FEV1 (data not presented)

Appears to be safe and reasonably well tolerated

REFERENCES

Bals R, Hubert D, Tümmler B. Antibiotic treatment of CF lung disease: From bench to bedside. J Cystic Fibrosis 2011; 10 Suppl 2: S146-S151.

Besouw M, Masereeuw R, van den Heuvel L, Levtchenko E. Cysteamine: an old drug with new potential. Drug Discovery Today 2013, 18; 15/16: 785-92.

Britto M T, Kotagal U R, Hornung R W, et al. Impact of recent pulmonary exacerbations on quality of life in patients with cystic fibrosis. Chest 2002; 121:64-72.

Goss C H, Burns J L. Exacerbations in cystic fibrosis. 1: Epidemiology and pathogenesis. Thorax 2007; 62:360-367.

Goss C H, Quittner A L. Patient-reported outcomes in cystic fibrosis. Proc Am Thorac Soc 2007; 4:378-386.

Giwercman B, Lambert P A, Rosdahl V T, Shand G H, Hoiby N. Rapid emergence of resistance in Pseudomonas aeruginosa in cystic fibrosis patients due tot in vivo selection of stable partially derepressed B-lactamase producing strains. J Antimicrobial Chemo 1990; 26: 247-59.

Hegarty M, MacDonald J, Watter P, Wilson C. Quality of life in young people with cystic fibrosis: effects of hospitalization, age and gender, and differences in parent/child perceptions. Child: Care, Health Develop 2009; 35:462-468.

Hoiby N. New antimicrobials in the management of cystic fibrosis. J Antimicrobial Chem, 2002; 49:235-238.

Hudzicki Kirby-Bauer Disk Diffusion Susceptibility Test Protocol, American Society for Microbiology, 2009; 1-23

Koch C, Pedersen S, Jensen E, et al. Retrospective clinical study of hypersensitivity reactions to aztreonam and six other beta-lactam antibiotics in cystic fibrosis patients receiving multiple treatment courses. Rev Infect Dis 1991; 13:5608-11.

Oliver A, Canton R, Campo P, Baquero F, Blazquez J. High frequency of hypermutatable Pseudomonas aeruginosa in cystic fibrosis lung infection. Science 2000; 288:1251-3.

Pitt T L, Sparrow M, Warner M, Stefanidou M. Survey of resistance of Pseudomonas aeruginosa from UK patients with cystic fibrosis to six commonly prescribed antimicrobial agents. Thorax 2003; 58:794-6.

Pleasants R, Samuelson W. Allergic reactions to parenteral beta-lactam antibiotics in patients with cystic fibrosis. Chest 1994; 106:1124-8.

Sanders D B, Bittner R C L, Rosenfeld M, et al. Failure to recover to baseline pulmonary function after cystic fibrosis pulmonary exacerbation. Am J Respir Crit Care Med 2010; 182:627-632.

Sanders D B, Bittner R C L, Rosenfeld M, et al. Pulmonary exacerbations are associated with subsequent FEV1 decline in both adults and children with cystic fibrosis. Pediatr Pulmonol 2011; 46:393-400.

Stewart P S, Costerton J W. Antibiotic resistance of bacteria in biofilms. Lancet 2007; 358:135-8.

UK CF Registry, Annual Data Report 2014 http://www.cysticfibrosis.org.uk/media/598466/annual-data-report-2013-jul14.pdf Wills R, Henry R L, J Francis. Antibiotic hypersensitivity reactions in cystic fibrosis. J Paediatr Child Health 1998; 43:325-9.

The invention claimed is:

1. A method of treating pulmonary exacerbations in cystic fibrosis, the method comprising administering to a patient in need thereof, cysteamine, or a pharmaceutically acceptable salt thereof, bi-daily as two sub-doses to form a total daily dose, wherein each sub-dose is in a range of 400 to 600 mg and the bidaily sub-doses are administered 8-12 hours apart, wherein the patient in need thereof exhibits pulmonary exacerbations in cystic fibrosis and wherein the treating relates to imparting a benefit to patients afflicted with cystic fibrosis or a condition associated with cystic fibrosis.

2. The method of claim 1, wherein the total daily dose is in the range: a) 800-1000 mg; or b) 850-950 mg.

3. The method of claim 1, wherein the total daily dose is administered in equal divided sub-doses.

4. The method of claim 1, wherein the total daily dose is 900 mg administered as two sub-doses of 450 mg each.

5. The method of claim 1, wherein bi-daily sub-doses are administered 12 hours apart.

6. The method of claim 1, wherein the cysteamine is administered as an oral dose.

7. The method of claim 6, wherein the oral dose is: a) a liquid; or b) a solid.

8. The method of claim 1, wherein the pharmaceutically acceptable salt is cysteamine bitartrate.

9. The method of claim 1, wherein the cysteamine, or a pharmaceutically acceptable salt thereof, is in the form of a composition comprising cysteamine, or a pharmaceutically acceptable salt thereof, and one or more selected from the list of: carriers, excipients, diluents, adjuvants and antimicrobial agents.

10. The method of claim 1, wherein the method is provided as an adjunct therapy.

11. The method of claim 1, wherein each sub-dose is provided as a single unit dose.

* * * * *